(12) United States Patent
Stewart et al.

(10) Patent No.: US 11,149,024 B2
(45) Date of Patent: Oct. 19, 2021

(54) SYNTHESIS OF MCL-1 INHIBITOR

(71) Applicant: ASTRAZENECA AB

(72) Inventors: Craig Robert Stewart, Macclesfield (GB); Simon Hardy, Macclesfield (GB); Andrew Stark, Macclesfield (GB); Alexander Hird, Waltham, MA (US); Qing Ye, Waltham, MA (US); Xiaolan Zheng, Waltham, MA (US); Cati Ferrar, Groningen (NL); Jan Koek, Groningen (NL); Debasis Hazra, Louisville, KY (US)

(73) Assignee: ASTRAZENECA AB, Sodertalje (SE)

( * ) Notice: Subject to any disclaimer, the term of this patent is extended or adjusted under 35 U.S.C. 154(b) by 94 days.

(21) Appl. No.: 16/497,919

(22) PCT Filed: Mar. 29, 2018

(86) PCT No.: PCT/EP2018/058056
§ 371 (c)(1),
(2) Date: Sep. 26, 2019

(87) PCT Pub. No.: WO2018/178227
PCT Pub. Date: Oct. 4, 2018

(65) Prior Publication Data

US 2021/0122735 A1    Apr. 29, 2021

Related U.S. Application Data

(60) Provisional application No. 62/479,493, filed on Mar. 31, 2017.

(51) Int. Cl.
*C07D 403/04* (2006.01)
*C07C 251/76* (2006.01)
*C07D 231/12* (2006.01)

(52) U.S. Cl.
CPC .......... *C07D 403/04* (2013.01); *C07C 251/76* (2013.01); *C07D 231/12* (2013.01)

(58) Field of Classification Search
CPC ... C07D 403/04; C07D 231/12; C07D 251/76
See application file for complete search history.

(56) References Cited

U.S. PATENT DOCUMENTS

2016/0106731 A1* 4/2016 Lee .................. C07D 498/06
514/211.12

FOREIGN PATENT DOCUMENTS

WO        2017182625 A1    10/2017
WO    WO-2017182625 A1 * 10/2017 .............. A61P 35/02

* cited by examiner

*Primary Examiner* — Matthew P Coughlin

(57) ABSTRACT

Disclosed are intermediates and methods of synthesizing Compound 1.

Compound (1)

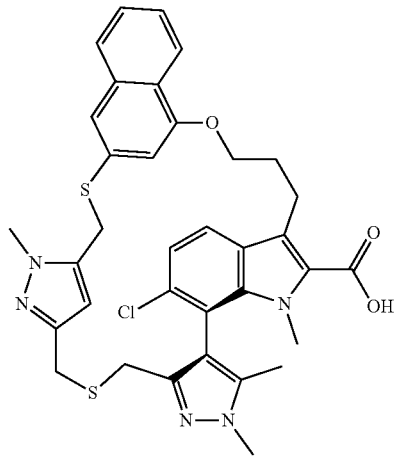

2 Claims, 2 Drawing Sheets

SYNTHESIS OF MCL-1 INHIBITOR

BACKGROUND

Myeloid Cell Leukemia 1 (Mcl-1) is an important anti-apoptotic member of the BCL-2 family of proteins and a master regulator of cell survival. Amplification of the MCL1 gene and/or overexpression of the Mcl-1 protein has been observed in multiple cancer types and is commonly implicated in tumor development. In fact, MCL1 is one of the most frequently amplified genes in human cancer. In many malignancies, Mcl-1 is a critical survival factor and it has been shown to mediate drug resistance to a variety of anti-cancer agents.

Mcl-1 promotes cell survival by binding to pro-apoptotic proteins like Bim, Noxa, Bak, and Bax and neutralizing their death-inducing activities. Inhibition of Mcl-1 thereby releases these pro-apoptotic proteins, often leading to the induction of apoptosis in tumor cells dependent on Mcl-1 for survival. Therapeutically targeting Mcl-1 alone or in combination with other therapies, therefore, is a promising strategy to treat a multitude of malignancies and to overcome drug resistance in many human cancers. The compound chemically named $(R_a)$-(+)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (referred to as Compound 1):

Compound 1

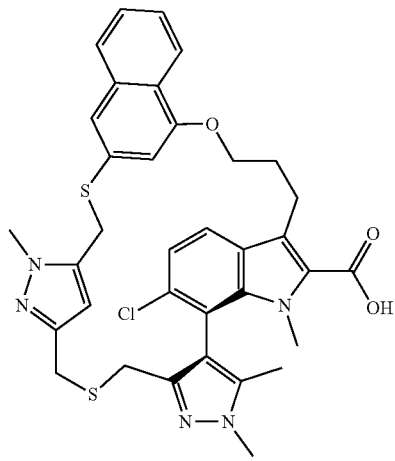

is a potent Mcl-1 inhibitor, as described in more detail below. Accordingly, there is a need to develop new methods for synthesizing Compound I in an efficient manner.

BRIEF SUMMARY

Provided herein are processes and intermediates useful for the synthesis of Compound 1:

Compound 1

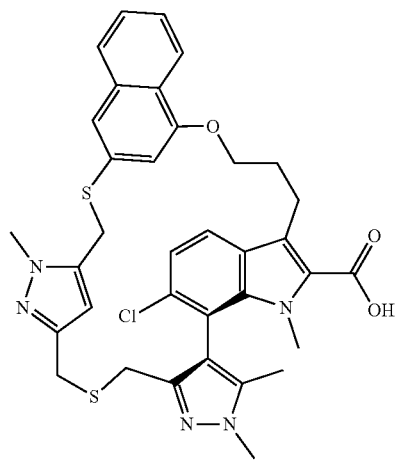

In some embodiments, disclosed are the following intermediates, and any salts thereof, and the synthesis thereof:

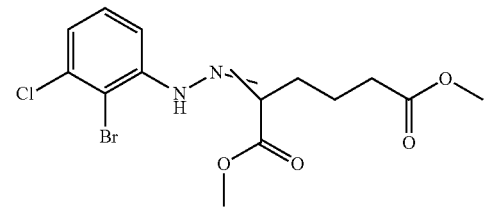

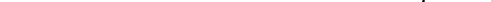

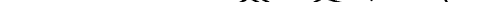

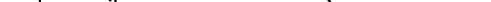

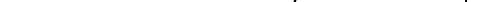

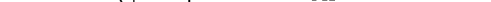

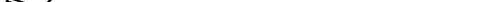

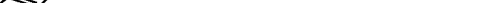

-continued

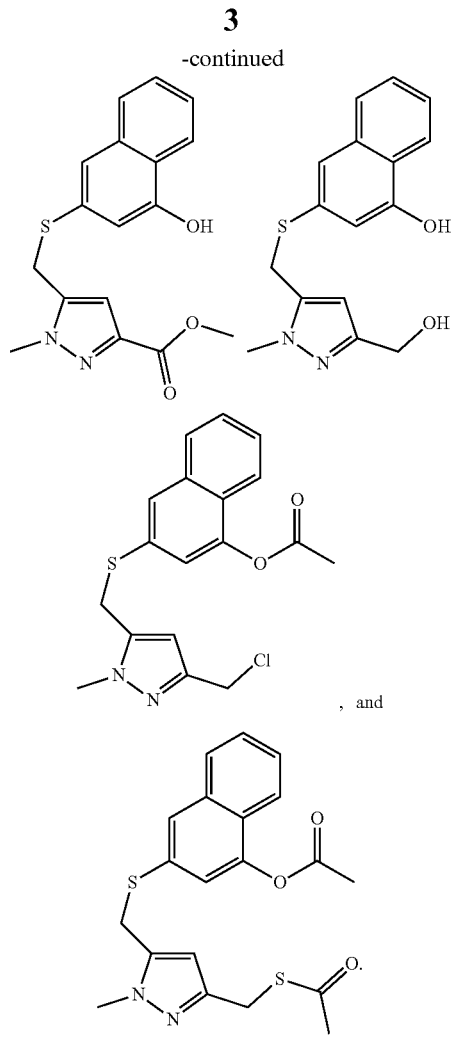

, and

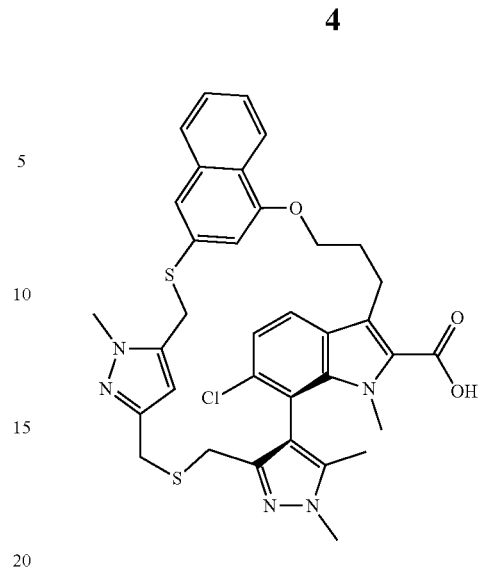

Compound 1

Compound 1 is a potent Mcl-1 inhibitor as illustrated in Example 1, infra, and may be useful in the treatment of cancer, including hematological malignancies such as acute myeloid leukemia, multiple myeloma, mantle cell lymphoma, chronic lymphocytic leukemia, diffuse large B cell lymphoma, Burkitt's lymphoma, follicular lymphoma and solid tumors, for example, non-small cell lung cancer (NSCLC), small cell lung cancer (SCLC), breast cancer, neuroblastoma, prostate cancer, melanoma, pancreatic cancer, uterine, endometrial and colon cancer. Due to Compound 1's structural complexity, arriving at an efficient synthesis may be an important aspect in developing Compound 1 as a potential cancer treatment.

Intermediates

In some embodiments, disclosed is (E/Z)-dimethyl 2-(2-(2-bromo-3-chlorophenyl)hydrazono)hexanedioate (Intermediate 1):

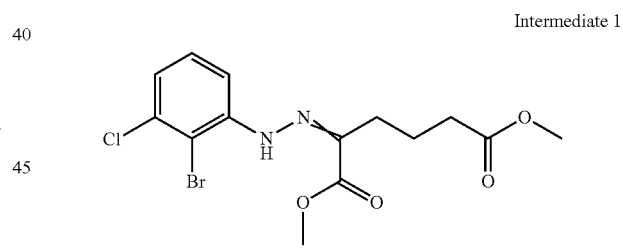

Intermediate 1

In some embodiments, disclosed is a compound of formula (d):

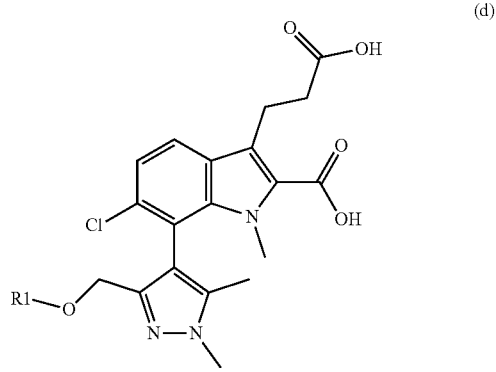

(d)

DETAILED DESCRIPTION

Figure 1:
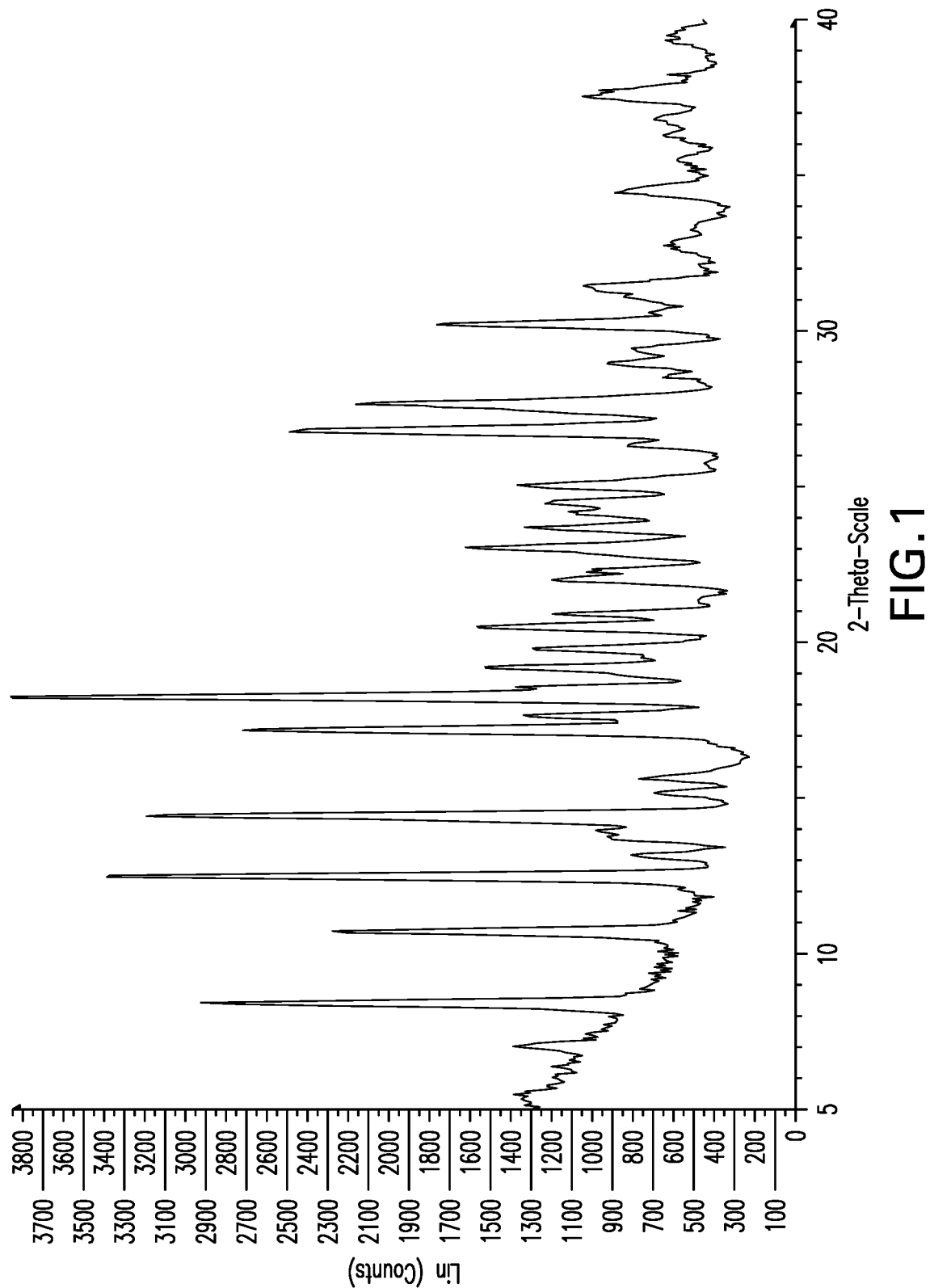
FIG. 1 illustrates the powder X-ray diffraction diagram of Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate.

In some embodiments, provided herein are processes and intermediates useful for the synthesis of $(R_a)$-(+)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid (Compound 1):

wherein R1 is a protecting group or hydrogen. In some embodiments, R1 is p-methoxybenzyl. In some embodiments, the compound of formula (a) is (±)-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid (Intermediate 6):

Intermediate 6

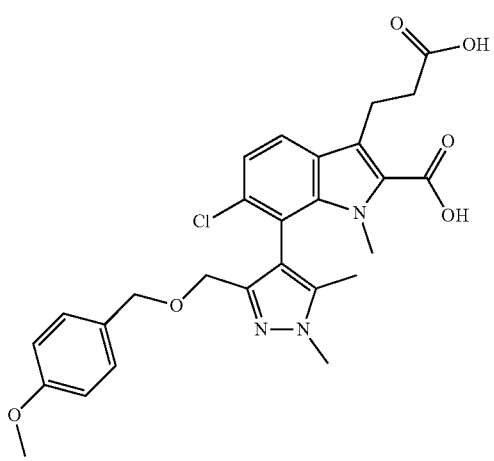

In some embodiments, disclosed is a compound of formula (e):

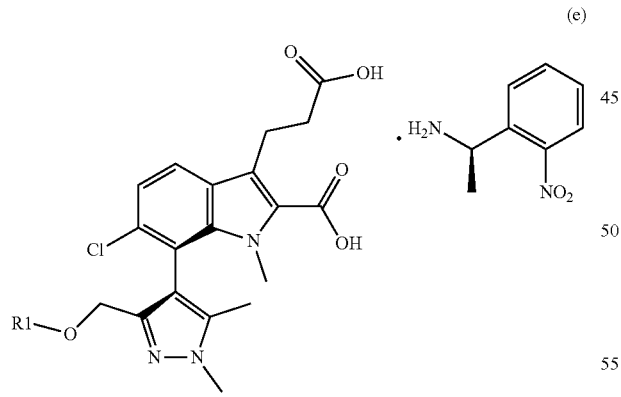

(e)

wherein R1 is a protecting group or hydrogen. In some embodiments, R1 is p-methoxybenzyl. In some embodiments, the compound of formula (b) is (R$_a$)-3-(2-Carboxyethyl)-6-chloro-7-(3-(((4-methoxybenzyl)oxy)methyl)-1,5-dimethyl-1H-pyrazol-4-yl)-1-methyl-1H-indole-2-carboxylic acid-(1R)-1-(2-nitrophenyl)ethanamine (1:1 salt) (Intermediate 7):

Intermediate 7

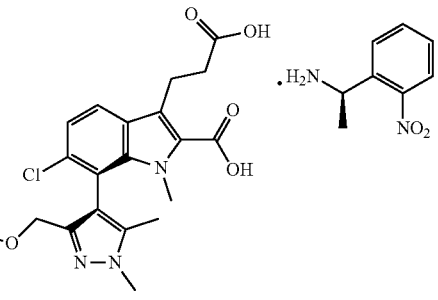

In some embodiments, disclosed is methyl 5-(((4-hydroxynaphthalen-2-yl)thio)methyl)-1-methyl-1H-pyrazole-3-carboxylate (Intermediate 12):

Intermediate 12

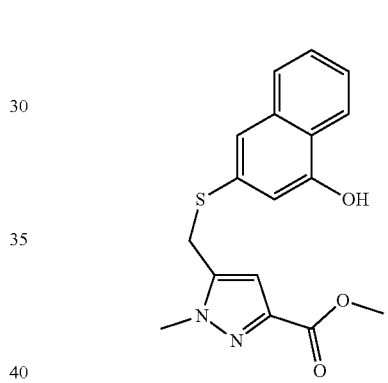

In some embodiments, disclosed is a 3-(((3-(hydroxymethyl)-1-methyl-1H-pyrazol-5-yl)methyl)thio)naphthalen-1-ol (Intermediate 13):

Intermediate 13

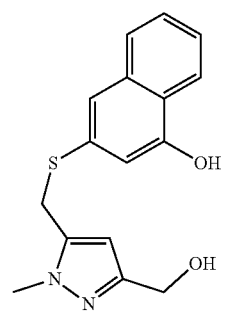

In some embodiments, disclosed is 3-(((3-(chloromethyl)-1-methyl-1H-pyrazol-5-yl)methyl)thio)naphthalen-1-ol (Intermediate 14):

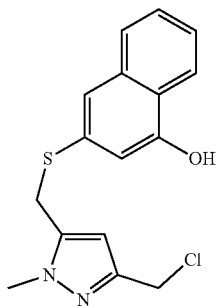

Intermediate 14

In some embodiments, disclosed is 3-(((3-(chloromethyl)-1-methyl-1H-pyrazol-5-yl)methyl)thio)naphthalen-1-yl acetate (Intermediate 15):

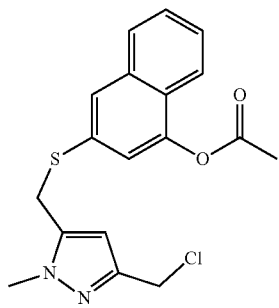

Intermediate 15

In some embodiments, disclosed is 3-(((3-((acetylthio)methyl)-1-methyl-1H-pyrazol-5-yl)methyl)thio)naphthalen-1-yl acetate (Intermediate 16):

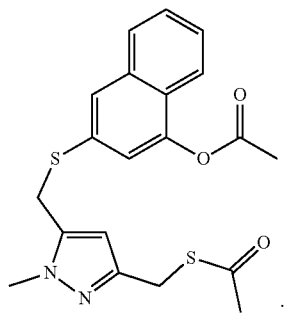

Intermediate 16

Synthesis

In some embodiments, disclosed is a method of synthesizing (E/Z)-dimethyl 2-(2-(2-bromo-3-chlorophenyl)hydrazono)hexanedioate (Intermediate 1):

Intermediate 1

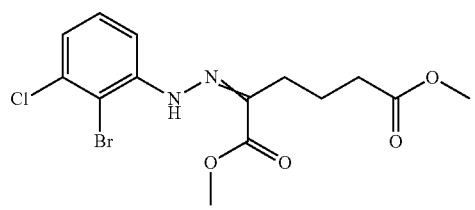

comprising the steps of (i) contacting 2-bromo-3-chloroaniline with methyl 2-oxocyclopentane-1-carboxylate with a diazotization agent in an acidic aqueous system; (ii) adding methyl 2-oxocyclopentane-1-carboxylate and an aqueous base to the acidic aqueous system; (iii) isolating the resulting hydrazone; (iv) contacting the hydrazone with an acidic solution; and (v) isolating (E/Z)-dimethyl 2-(2-(2-bromo-3-chlorophenyl)hydrazono)hexanedioate (Intermediate 1). In some embodiments, the diazotization agent is $NaNO_2$, $Ca(NO_2)_2$ or $KNO_2$. In some embodiments, the diazotization agent is $NaNO_2$. In some embodiments, the acidic aqueous system comprises a protic acid and water. In some embodiments, the protic acid is hydrochloric acid. In some embodiments, the aqueous base is potassium acetate, potassium hydroxide, sodium hydroxide, potassium carbonate, sodium carbonate or potassium phosphate. In some embodiments the aqueous base is potassium acetate. In some embodiments, the acidic solution comprises an acid and an alcohol. In some embodiments, the acidic solution comprises concentrated sulfuric acid and methanol, methanesulfonic acid and methanol or p-toluenesulfonic acid and methanol. In some embodiments, the acidic solution comprises concentrated sulfuric acid and methanol.

In some embodiments, disclosed is a method of synthesizing methyl 7-bromo-6-chloro-3-(3-methoxy-3-oxopropyl)-1H-indole-2-carboxylate (Intermediate 2):

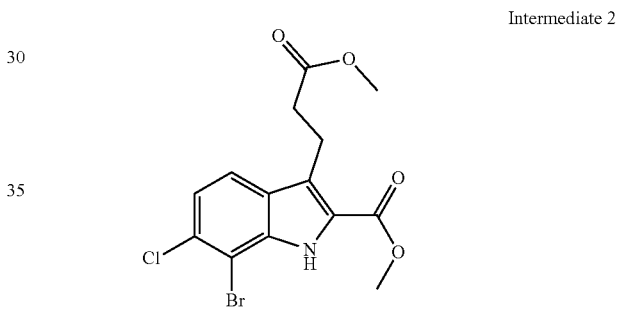

Intermediate 2 comprising the steps of (i) contacting (E/Z)-dimethyl 2-(2-(2-bromo-3-chlorophenyl)hydrazono)hexanedioate (Intermediate 1) with an acidic solution; and (ii) isolating methyl 7-bromo-6-chloro-3-(3-methoxy-3-oxopropyl)-1H-indole-2-carboxylate (Intermediate 2). In some embodiments, the acidic solution comprises an acid and an alcohol. In some embodiments, the acidic solution comprises concentrated sulfuric acid and methanol, methanesulfonic acid and methanol or p-toluenesulfonic acid and methanol. In some embodiments, the acidic solution comprises concentrated sulfuric acid and methanol. In some embodiment, the method of synthesizing Intermediate 2 further comprises the step of heating the acidic solution prior to isolating Intermediate 2.

In some embodiments, disclosed is a method of synthesizing a compound of formula (a):

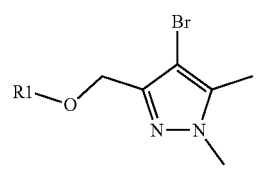

(a)

wherein R1 is a protecting group or hydrogen, comprising the steps of: (i) contacting ethyl 1,5-dimethyl-1H-pyrazole-3-carboxylate with a reducing agent in the presence of a first solvent to form a first solution; (ii) isolating (1,5-dimethyl-1H-pyrazol-3-yl)methanol; (iii) contacting (1,5-dimethyl-1H-pyrazol-3-yl)methanol with a brominating agent in the presence of a second solvent to form (4-bromo-1,5-dimethyl-1H-pyrazol-3-yl)methanol; (iv) isolating (4-bromo-1,5-dimethyl-1H-pyrazol-3-yl)methanol; (v) contacting (4-bromo-1,5-dimethyl-1H-pyrazol-3-yl)methanol with a base, optionally a phase transfer catalyst, and a protecting group precursor in a third solvent; and (v) isolating the compound of formula (a). In some embodiments, the reducing agent is selected from lithium aluminum hydride (LAH), diisobutylaluminum hydride (DIBAL), lithium borohydride (LiBH$_4$), sodium bis(2-methoxyethoxy)aluminum hydride (Red-Al®) and sodium borohydride (NaBH$_4$). In some embodiments, the reducing agent is lithium aluminum hydride. In some embodiments, the first solvent is selected from toluene, THF, 2-methyltetrahydrofuran, MTBE, methanol, ethanol and diethyl ether. In some embodiments, the first solvent is tetrahydrofuran. In some embodiments, the second solvent is tetrahydrofuran. In some embodiments, the brominating agent is 1,3-dibromo-5,5-dimethylhydantoin (DBDMH). In some embodiments, the brominating agent is N-bromosuccinimide. In some embodiments, the base is lithium hydroxide, sodium hydroxide, potassium hydroxide, sodium hydride, lithium hydride or potassium hydride. In some embodiments, a phase transfer catalyst is used, for example Bu$_4$N.HSO$_4$ or benzyltrimethylammonium chloride. In some embodiments the base is potassium hydroxide and the phase transfer catalyst is tetrabutylammonium bisulfate. In some embodiments, the protecting group precursor is 1-(chloromethyl)-4-methoxybenzene. In some embodiments, R1 is p-methoxybenzyl. In some embodiments, the compound of formula (a) is 4-bromo-3-(((4-methoxybenzyl)oxy)methyl)-1,5-dimethyl-1H-pyrazole (Intermediate 3):

Intermediate 3

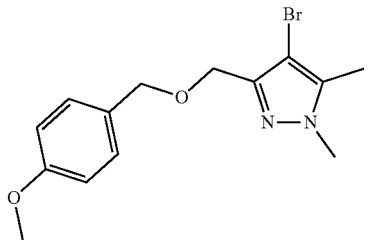

In some embodiments, disclosed is a method of synthesizing a compound of formula (b):

(b)

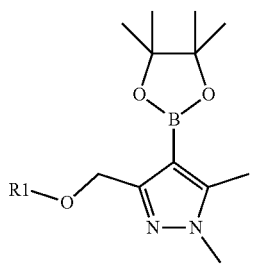

wherein R1 is a protecting group or hydrogen, comprising the steps of: (i) contacting a compound of formula (a) with a metalating agent in the presence of a solvent; (ii) adding 2-isopropoxy-4,4,5,5-tetramethyl-1,3,2-dioxaborolane; (iii) adding an acidic solvent solution; and (iv) isolating the compound of formula (b). In some embodiments, the metalating agent is n-butyl lithium. In some embodiments, the solvent is tetrahydrofuran. In some embodiments, the acidic solvent solution comprises acetic acid and toluene. In some embodiments, R1 is p-methoxybenzyl. In some embodiments, the compound of formula (a) is 4-bromo-3-(((4-methoxybenzyl)oxy)methyl)-1,5-dimethyl-1H-pyrazole (Intermediate 3). In some embodiments, the compound of formula (b) is 3-(((4-methoxybenzyl)oxy)methyl)-1,5-dimethyl-4-(4,4,5,5-tetramethyl-1,3,2-dioxaborolan-2-yl)-1H-pyrazole (Intermediate 4):

Intermediate 4

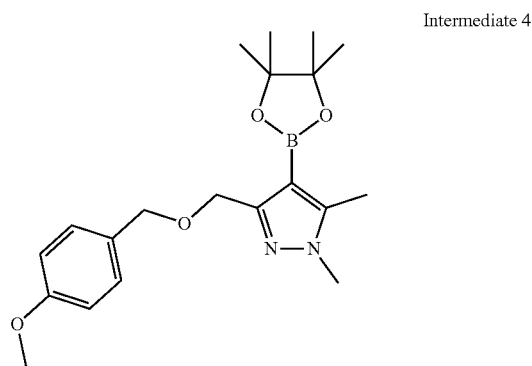 [SMILES: COc1ccc(COCc2nn(C)c(C)c2B2OC(C)(C)C(C)(C)O2)cc1]

In some embodiments, disclosed is a method of synthesizing a compound of formula (c):

(c)

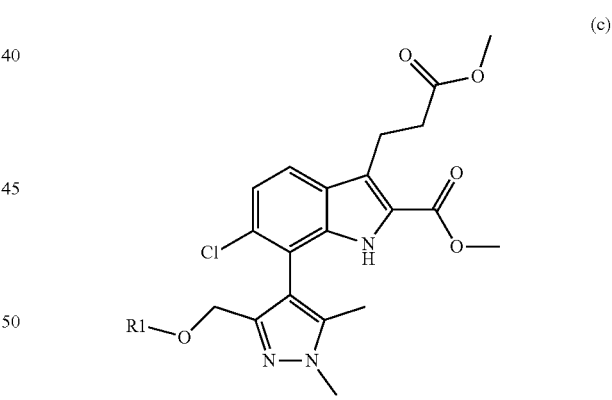

wherein R1 is a protecting group or hydrogen, comprising the steps of: (i) contacting a compound of formula (b) with methyl 7-bromo-6-chloro-3-(3-methoxy-3-oxopropyl)-1H-indole-2-carboxylate (Intermediate 2) with a palladium catalyst in the presence of a base and solvent; and (ii) isolating the compound of formula (c). In some embodiments, the palladium catalyst is selected from tetrakis(triphenylphosphine)palladium(0), bis(di-tert-butyl(4-dimethylaminophenyl)phosphine)dichloropalladium(II) and 1,1'-bis(di-tert-butylphosphino)ferrocene palladium dichloride. In some embodiments the base is potassium carbonate or potassium phosphate. In some embodiments, the palladium catalyst is 1,1'-bis(di-tert-butylphosphino)ferrocene palladium dichloride. In some embodiments, the solvent is dioxane, water or a combination thereof. In some embodiments, R1 is p-methoxybenzyl. In some embodiments the compound of formula (b) is 3-(((4-methoxybenzyl)oxy)methyl)-1,5-dimethyl-4-(4,4,5,5-tetramethyl-1,3,2-dioxaborolan-2-yl)-1H-pyrazole (Intermediate 4). In some embodiments, the compound of formula (c) is (±)-methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate (Intermediate 5):

In some embodiments, R1 is p-methoxybenzyl. In some embodiments, the compound of formula (c) is (±)-methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate (Intermediate 5). In some embodiments, the compound of formula (d) is (±)-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid (Intermediate 6):

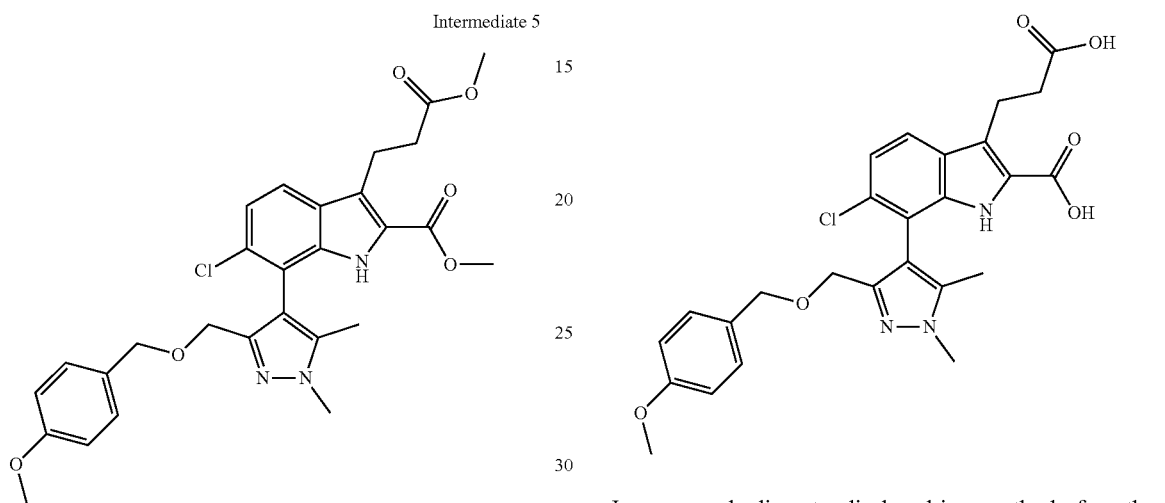

Intermediate 5

Intermediate 6

In some embodiments, disclosed is a method of synthesizing a compound of formula (d):

In some embodiments, disclosed is a method of synthesizing a compound of formula (e):

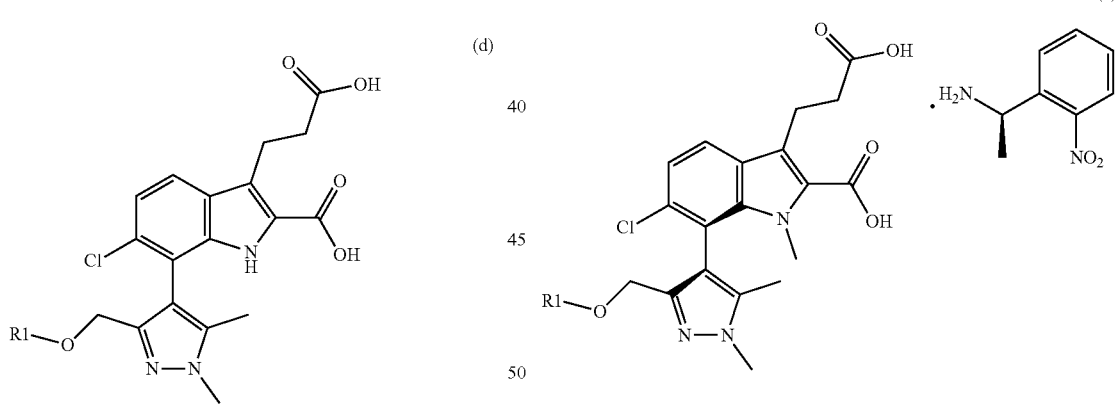

(d)

(e)

wherein R1 is a protecting group or hydrogen, comprising the steps of (i) contacting a compound of formula (c) with a methylating agent in a solvent; (ii) treating the resulting methylated derivative with an ester hydrolysis reagent and (iii) isolating the compound of formula (d). In some embodiments, the compound of formula (c) is Intermediate 5. In some embodiments, the ester hydrolysis reagent is a hydroxide base selected from lithium hydroxide, potassium hydroxide and sodium hydroxide. In some embodiments, the methylating agent is selected from methyl iodide, dimethylsulfate and dimethyl formamide-dimethyl acetal (DMF-DMA). In some embodiments, the methylating agent is dimethyl formamide-dimethyl acetal. In some embodiments, the solvent is toluene.

wherein R1 is a protecting group or hydrogen, comprising the steps of: (i) contacting a compound of formula (d) with (1R)-1-(2-nitrophenyl)ethanamine hydrochloride in the presence of a base and a solvent; and (ii) isolating the compound of formula (e). In some embodiments, the base is sodium hydroxide, potassium hydroxide, diisopropylethylamine or triethylamine. In some embodiments, the base is sodium hydroxide. In some embodiments, the solvent is water, THF, methanol, ethanol, isopropanol, n-butanol, methyl ethyl ketone or a combination thereof. In some embodiments, the solvent is water, ethanol or a combination thereof. In some embodiments, R1 is p-methoxybenzyl. In some embodiments, the compound of formula (d) is (±)-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid (Intermediate 6). In some embodiments, the compound of formula (e) is (R$_a$)-3-(2-Carboxyethyl)-6-chloro-7-(3-(((4-methoxybenzyl)oxy)methyl)-1,5-dimethyl-1H-pyrazol-4-yl)-1-methyl-1H-indole-2-carboxylic acid-(1R)-1-(2-nitrophenyl)ethanamine (1:1 salt) (Intermediate 7):

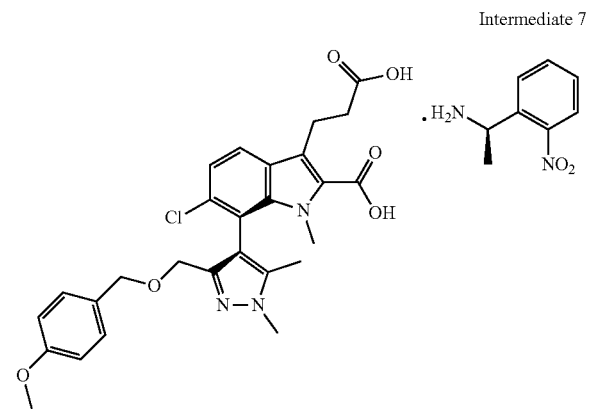

Intermediate 7

In some embodiments, disclosed is a method of synthesizing (R$_a$)-methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (Intermediate 8):

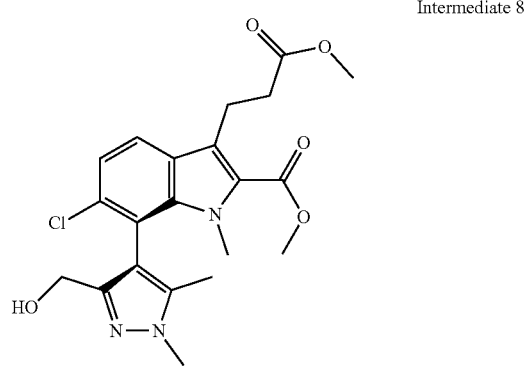

Intermediate 8 comprising the steps of (i) contacting a compound of formula (e) with an acid in the presence of a first solvent; (ii) isolating the free acid component of a compound of formula (e); (iii) treating the free acid with a methylating agent or methanol in a second solvent; (iv) removing the protecting group, optionally in a third solvent; and (v) isolating (R$_a$)-methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (Intermediate 8). In some embodiments, the compound of formula (e) is R$_a$-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid-(1R)-1-(2-nitrophenyl)ethanamine (1:1 salt) (Intermediate 7). In some embodiments, the first solvent is tetrahydrofuran, toluene or a combination thereof. In some embodiments, the methylating agent is DMF-DMA. In some embodiments, the second solvent is toluene. In some embodiments, the third solvent is methanol. In some embodiments, the protecting group is removed by acetyl chloride. In some embodiments, the protecting group is removed by acetyl chloride in methanol. In some embodiments, the protecting group is removed by an acid, for example, hydrochloric acid formed in situ via reaction of acetyl chloride with methanol.

In some embodiments, disclosed is a method of synthesizing (R$_a$)-methyl 6-chloro-7-(3-(hydroxymethyl)-1,5-dimethyl-1H-pyrazol-4-yl)-3-(3-hydroxypropyl)-1-methyl-1H-indole-2-carboxylate (Intermediate 9):

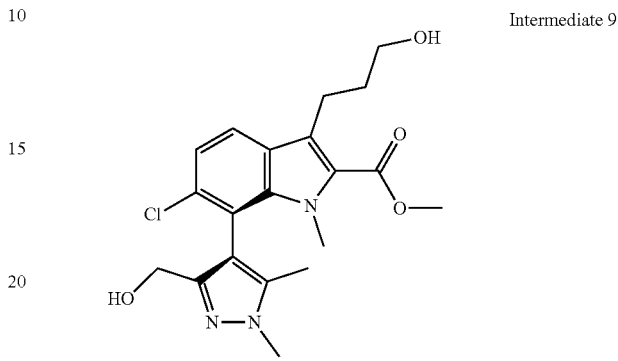

Intermediate 9 comprising the steps of (i) contacting (R$_a$)-methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (Intermediate 8) with a reducing agent in the presence of a solvent; and (ii) isolating (R$_a$)-methyl 6-chloro-7-(3-(hydroxymethyl)-1,5-dimethyl-1H-pyrazol-4-yl)-3-(3-hydroxypropyl)-1-methyl-1H-indole-2-carboxylate (Intermediate 9). In some embodiments, the reducing agent is diisobutyl aluminum hydride. In some embodiments, the solvent is THF, hexane or a combination thereof.

In some embodiments, disclosed is a method of synthesizing methyl 5-(chloromethyl)-1-methyl-1H-pyrazole-3-carboxylate (Intermediate 10):

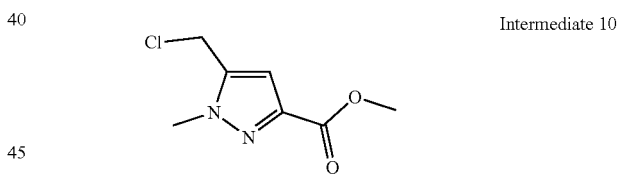

Intermediate 10 comprising the steps of (i) contacting dimethyl 1-methyl-1H-pyrazole-3,5-dicarboxylate with a reducing agent in the presence of a solvent; (ii) isolating methyl 3-(hydroxymethyl)-1-methyl-1H-pyrazole-5-carboxylate; (iii) contacting methyl 3-(hydroxymethyl)-1-methyl-1H-pyrazole-5-carboxylate with a chlorinating agent; and (iv) isolating methyl 5-(chloromethyl)-1-methyl-1H-pyrazole-3-carboxylate (Intermediate 10). In some embodiments, the solvent is a mixture of methanol and 2-methyltetrahydrofuran. In some embodiments, the reducing agent is sodium borohydride or lithium borohydride. In some embodiments the reducing agent is sodium borohydride. In some embodiments the solvent is methanol, ethanol, water, 2-methyltetrahydrofuran, dimethylacetamide, DCM, THF, cyclopentyl methyl ether, acetonitrile or a mixture thereof. In some embodiments, the solvent is a mixture of methanol and 2-methyltetrahydrofuran.

In some embodiments, disclosed is a method of synthesizing 3-(acetylthio)naphthalen-1-yl acetate (Intermediate 11):

Intermediate 11

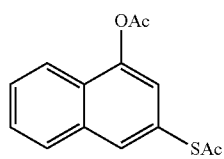

comprising the steps of (i) contacting sodium 4-hydroxynapthalene-2-sulfonate with triphenylphosphine and iodine in a solvent; (ii) isolating 3-mercaptonaphthalen-1-ol; (iii) contacting 3-mercaptonaphthalen-1-ol with an acylating agent in the presence of an amine base and a nucleophilic catalyst; and (iv) isolating 3-(acetylthio)naphthalen-1-yl acetate (Intermediate 11). In some embodiments, the solvent is acetonitrile. In some embodiments, the acylating agent is acetic anhydride or acetyl chloride. In some embodiments, the acylating agent is acetic anhydride. In some embodiments, the amine base is selected from triethylamine, pyridine or diisopropylethylamine. In some embodiments, the amine base is triethylamine. In some embodiments, the nucleophilic catalyst is selected from 4-dimethylaminopyridine, pyridine and N-methylimidazole. In some embodiments, the nucleophilic catalyst is 4-dimethylaminopyridine.

In some embodiments, disclosed is a method of synthesizing methyl 5-(((4-hydroxynaphthalen-2-yl)thio)methyl)-1-methyl-1H-pyrazole-3-carboxylate (Intermediate 12):

Intermediate 12

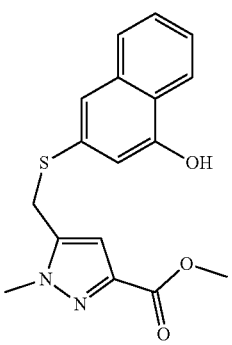

comprising the steps of (i) contacting 3-(acetylthio)naphthalen-1-yl acetate (Intermediate 11) with methyl 5-(chloromethyl)-1-methyl-1H-pyrazole-3-carboxylate (Intermediate 10) in the presence of a base and a solvent; and (ii) isolating 5-(((4-hydroxynaphthalen-2-yl)thio)methyl)-1-methyl-1H-pyrazole-3-carboxylate (Intermediate 12). In some embodiments, the base is selected from potassium carbonate, lithium hydroxide, 1,8-diazabicyclo[5.4.0]undec-7-ene, sodium hydroxide, potassium hydroxide and sodium ethoxide. In some embodiments, the base is potassium carbonate. In some embodiments, the solvent is selected from methanol, ethanol, water and combinations thereof. In some embodiments, the solvent is methanol.

In some embodiments, disclosed is a method of synthesizing 3-(((3-(hydroxymethyl)-1-methyl-1H-pyrazol-5-yl)methyl)thio)naphthalen-1-ol (Intermediate 13):

Intermediate 13

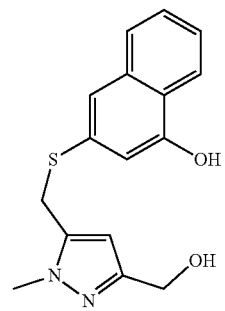

comprising the steps of (i) contacting methyl 5-(((4-hydroxynaphthalen-2-yl)thio)methyl)-1-methyl-1H-pyrazole-3-carboxylate (Intermediate 12) with a reducing agent in a solvent; and (ii) isolating 3-(((3-(hydroxymethyl)-1-methyl-1H-pyrazol-5-yl)methyl)thio)naphthalen-1-ol (Intermediate 13). In some embodiments, the reducing agent is diisobutylaluminum hydride. In some embodiments, the solvent is tetrahydrofuran, hexanes or a combination thereof.

In some embodiments, disclosed is a method of synthesizing 3-(((3-(chloromethyl)-1-methyl-1H-pyrazol-5-yl)methyl)thio)naphthalen-1-ol (Intermediate 14):

Intermediate 14

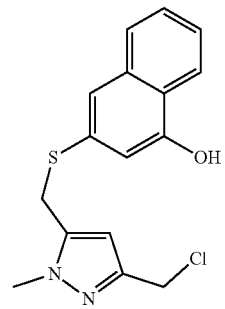

comprising the steps of (i) contacting 3-(((3-(hydroxymethyl)-1-methyl-1H-pyrazol-5-yl)methyl)thio)naphthalen-1-ol (Intermediate 13) with a chlorinating agent; and (ii) isolating 3-(((3-(chloromethyl)-1-methyl-1H-pyrazol-5-yl)methyl)thio)naphthalen-1-ol (Intermediate 14). In some embodiments, the solvent is selected from THF, dichloromethane, dimethylformamide and combinations thereof. In some embodiments, the solvent is dimethylformamide. In some embodiments, the chlorinating agent is methanesulfonyl chloride or thionyl chloride. In some embodiments, the chlorinating agent is methanesulfonyl chloride. In some embodiments, step (i) further comprises lithium chloride.

In some embodiments, disclosed is a method of synthesizing 3-(((3-(chloromethyl)-1-methyl-1H-pyrazol-5-yl)methyl)thio)naphthalen-1-yl acetate (Intermediate 15):

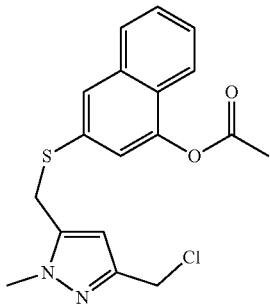

Intermediate 15 comprising the steps of (i) contacting 3-(((3-(chloromethyl)-1-methyl-1H-pyrazol-5-yl)methyl)thio)naphthalen-1-ol (Intermediate 14) with acetic anhydride, optionally an amine base, and a nucleophilic catalyst in a solvent; and (ii) isolating 3-(((3-(chloromethyl)-1-methyl-1H-pyrazol-5-yl)methyl)thio)naphthalen-1-yl acetate (Intermediate 15). In some embodiments, the amine base is triethylamine. In some embodiments the nucleophilic catalyst is selected from 4-dimethylaminopyridine, N-methylimidazole or pyridine. In some embodiments, the nucleophilic catalyst is 4-dimethylaminopyridine. In some embodiments, the solvent is acetonitrile.

In some embodiments, disclosed is a method of synthesizing 3-(((3-((acetylthio)methyl)-1-methyl-1H-pyrazol-5-yl)methyl)thio)naphthalen-1-yl acetate (Intermediate 16):

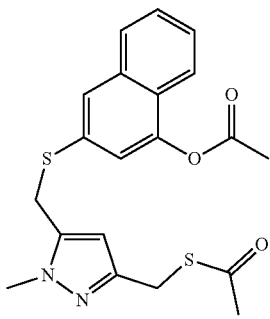

Intermediate 16 comprising the steps of (i) contacting 3-(((3-(chloromethyl)-1-methyl-1H-pyrazol-5-yl)methyl)thio)naphthalen-1-yl acetate (Intermediate 15) with potassium thioacetate in a solvent; and (ii) isolating 3-(((3-((acetylthio)methyl)-1-methyl-1H-pyrazol-5-yl)methyl)thio)naphthalen-1-yl acetate (Intermediate 16). In some embodiments, the solvent is acetonitrile.

In some embodiments, disclosed is a method of synthesizing $(R_a)$-(+)-methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylate

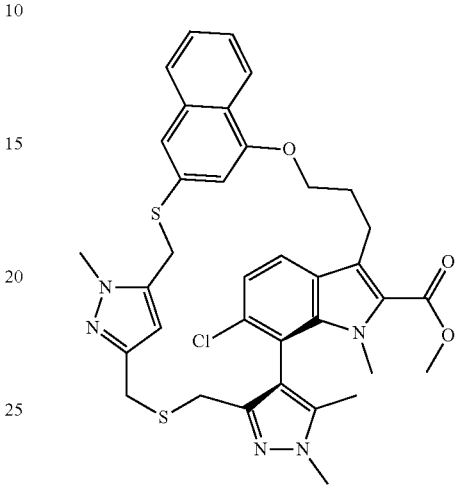

Intermediate 17 comprising the steps of: (i) contacting $(R_a)$-methyl 6-chloro-7-(3-(hydroxymethyl)-1,5-dimethyl-1H-pyrazol-4-yl)-3-(3-hydroxypropyl)-1-methyl-1H-indole-2-carboxylate (Intermediate 9) with a sulfonylating agent in the presence of an aprotic base and a solvent to form a first solution; (ii) adding an iodide salt to the first solution; (iii) isolating methyl 6-chloro-7-[3-(iodomethyl)-1,5-dimethyl-pyrazol-4-yl]-1-methyl-3-(3-methylsulfonyloxypropyl)indole-2-carboxylate; (iv) contacting 3-(((3-((acetylthio)methyl)-1-methyl-1H-pyrazol-5-yl)methyl)thio)naphthalen-1-yl acetate (Intermediate 16) with sodium methoxide in methanol to form a second solution; (v) adding methyl 6-chloro-7-[3-(iodomethyl)-1,5-dimethyl-pyrazol-4-yl]-1-methyl-3-(3-methylsulfonyloxypropyl)indole-2-carboxylate to the second solution; and (vi) isolating $(R_a)$-(+)-methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylate. In some embodiments, the aprotic base is diisopropylethylamine or N-methylmorpholine. In some embodiments, the aprotic base is diisopropylethylamine. In some embodiments, the sulfonylating agent is selected from methanesulfonyl anhydride, methanesulfonylchloride and p-toluenesulfonic anhydride. In some embodiments, the sulfonylating agent is methanesulfonyl anhydride. In some embodiments, the solvent is an aprotic solvent. In some embodiments, the aprotic solvent is tetrahydrofuran. In some embodiments, the iodide salt is lithium iodide.

In some embodiments, disclosed is a method of synthesizing Compound 1:

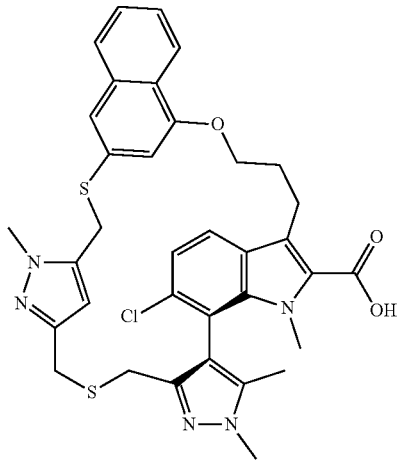

Compound 1

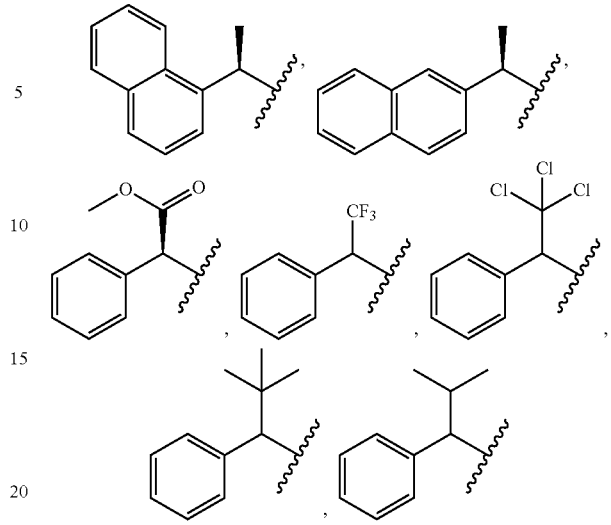

comprising the steps of (i) contacting (R$_a$)-(+)-methyl 17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$. 0$^{30,35}$]octatriaconta-1(37),4(38),6,11,14,16,18,20,23,29,31, 33,35-tridecaene-23-carboxylate with an ester hydrolysis reagent in a solvent and (ii) isolating (R$_a$)-(+)-17-chloro-5, 13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid. In some embodiments the ester hydrolysis reagent is a hydroxide base selected from lithium hydroxide, sodium hydroxide and potassium hydroxide. In some embodiments the base is sodium hydroxide. In some embodiments the solvent is selected from methanol, ethanol, isopropanol, DMSO, water and combinations thereof.

The term "isolated" means any appropriate method for obtaining a desired compound from the reaction mixture. The term "isolated" includes extraction, filtration, drying, crystallization, evaporation, chromatography (e.g., HPLC, column chromatography), metal scavenging and the like. The term "isolated" includes methods for obtaining unpurified and purified compounds from a reaction mixture. In some embodiments, a compound can be isolated from a reaction mixture by extraction and the next step in the reaction can be taken forward even though the compound hasn't been purified or removed from solvent. One of skill in the art would be able to determine the appropriate means of isolating a desired compound from the reaction mixture.

The term "protecting group" includes hydroxyl protecting groups, for example, benzyl, p-methoxybenzyl (PMB), tetrahydropyranyl (THP), p-methoxyphenyl (PMP) and t-butyldimethylsilyl (TBDMS),

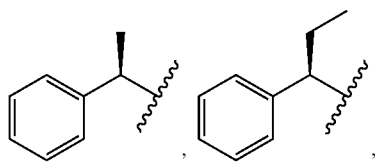

and the like. One of skill in the art would be able to identify appropriate hydroxyl protecting groups without undue experimentation.

The term "protecting group precursor" includes reagents that add protecting groups to a desired moiety. In some embodiments, the protecting group precursor is a hydroxyl protecting group precursor, for example, benzyl chloride, 4-methoxyphenol, bromomethylpyrazole, dihydropyran, p-methoxyphenol, chloromethylpyrazole, t-butyldimethylchlorosilane, t-butyldimethylchlorosilane and 1-(chloromethyl)-4-methoxybenzene. A skilled artisan would readily be able to identify the appropriate protecting group precursor without undue experimentation.

The term "reducing agent" includes lithium aluminum hydride, sodium borohydride, diisobutylaluminum hydride and the like.

The term "solvent" includes non-polar solvents, aprotic solvents and protic solvents. The term "non-polar solvent" includes pentane, cyclopentane, hexane, heptane, cyclohexane, benzene, toluene, chloroform, diethyl ether, cyclopentyl methyl ether, tert-butyl methyl ether, tert amyl methyl ether, dichloromethane and methyl ethyl ketone. The term "aprotic solvent" includes tetrahydrofuran, ethyl acetate, acetone, dimethylformamide, acetonitrile, 2-methyltetrahydrofuran, 1,4-dioxane, dimethylacetamide and dimethylsulfoxide. The term "protic solvent" includes n-butanol, isopropyl alcohol, n-propanol, ethanol, methanol, acetic acid and water. In some embodiments, the solvent may include combinations of any of the foregoing solvents. One of skill in the art would routinely be able to determine the appropriate solvent or solvent combinations for a particular reaction.

The term "brominating agent" includes 1,3-dibromo-5,5-dimethylhydantoin (DBDMH) and N-bromosuccinimide (NBS).

The term "diazotization agent" includes sodium nitrite (NaNO$_2$), calcium nitrite (Ca(NO$_2$)$_2$) and potassium nitrite (KNO$_2$).

The term "metalating agent" includes n-butyl lithium (n-BuLi).

The term "ester hydrolysis agent" includes sodium hydroxide (NaOH), potassium hydroxide (KOH), lithium hydroxide (LiOH), sodium chloride (NaCl) and lithium iodide (LiI).

The term "base" includes potassium acetate (KOAc), potassium carbonate ($K_2CO_3$), sodium carbonate ($Na_2CO_3$), potassium phosphate ($K_3PO_4$), potassium hydroxide, sodium hydroxide, sodium bis(trimethylsilyl)amide (NaHMDS), lithium bis(trimethylsilyl)amide (LiHMDS), sodium hydride (NaH), t-butyl ammonium bisulfate, n-butyl lithium, t-butyl lithium (t-BuLi), magnesium, zinc, lithium hydroxide, lithium diisopropyl amide (LDA), sodium amide ($NaNH_2$), potassium t-butoxide, pyridine, triethylamine (TEA), diisopropylethylamine (DIEA), 1,8-diazabicyclo[5.4.0]undec-7-ene (DBU), sodium methoxide (NaOMe) and sodium ethoxide (NaOEt). The term "base" also includes basic phase transfer catalysts, for example, tetrabutylammonium bisulfate ($Bu_4$-$HSO_4$), benzyltrimethylammonium chloride, polyethylene glycol and its derivatives, 18-crown-6 and other crown ethers.

The term "acid" includes hydrochloric acid (HCl), sulfuric acid ($H_2SO_4$), p-toluenesulfonic acid (p-TsOH), methanesulfonic acid and acetic acid. In some embodiments, the acid is concentrated.

The term "alcohol" includes methanol, ethanol, n-propanol, isopropanol, n-butanol, isobutanol and t-butyl alcohol.

The term "reducing agent" includes lithium aluminum hydride (LAH), borane-dimethylsulfide complex, borane-tetrahydrofuran complex, diisobutylaluminum hydride (DIBAL), lithium borohydride ($LiBH_4$), sodium bis(2-methoxyethoxy)aluminum hydride (Red-Al®) and sodium borohydride ($NaBH_4$).

The term "methylating agent" includes methyl iodide, dimethylsulfate and dimethyl formamide-dimethyl acetal (DMF-DMA).

The term "acylating agent" includes acetic anhydride and acetyl chloride.

The term "nucleophilic catalyst" includes dimethylaminopyridine (DMAP), pyridine and N-methylimidazole.

The term "amine base" includes triethylamine, pyridine and diisopropylethylamine.

The term "sulfonylating agent" includes tosic anhydride, methanesulfonyl chloride, p-toluenesulfonyl chloride and methanesulfonyl anhydride.

The term "iodide salt" includes lithium iodide, sodium iodide and potassium iodide.

In some embodiments, the term "palladium catalyst" includes 1,1'-bis(di-tert-butylphosphino)ferrocene palladium dichloride, [1,1'-bis(di-tert-butylphosphino)ferrocene] dichloropalladium(II) (Pd 188, $PdC_2$(dtbpf)), (R)-(−)-4,12-bis(diphenylphosphino)-[2.2]-paracyclophane (R-Phanephos), (S)-(−)-4,12-bis(diphenylphosphino)-[2.2]-paracyclophane (S-Phanephos), (2-Dicyclohexylphosphino-2',4',6'-triisopropyl-1,1'-biphenyl)[2-(2'-amino-1,1'-biphenyl)]palladium(II) methanesulfonate (XPhos-G3-Palladacycle, XPhos-Pd-G3), (2-Dicyclohexylphosphino-2',6'-diisopropoxy-1,1'-biphenyl)[2-(2'-amino-1,1'-biphenyl)]palladium(II) methanesulfonate (RuPhos-G3-Palladacycle, RuPhos-Pd-G3), (2-Dicyclohexylphosphino-2',6'-diisopropoxy-1,1'-biphenyl)[2-(2'-amino-1,1'-biphenyl)]palladium(II) methanesulfonate (RuPhos-G3-Palladacycle, RuPhos-Pd-G3), [(2-Di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos G3), tBuXPhos-Pd-G3, [(2-Di-tert-butylphosphino-2',4',6'-triisopropyl-1,1'-biphenyl)-2-(2'-amino-1,1'-biphenyl)] palladium(II) methanesulfonate (tBu XPhos G3), tetrakis(triphenylphosphine)palladium(0) and bis(di-tert-butyl(4-dimethylaminophenyl)phosphine)dichloropalladium(II)

In some embodiments, Compound 1 may be synthesized as set forth in Schemes I-VII:

Scheme I

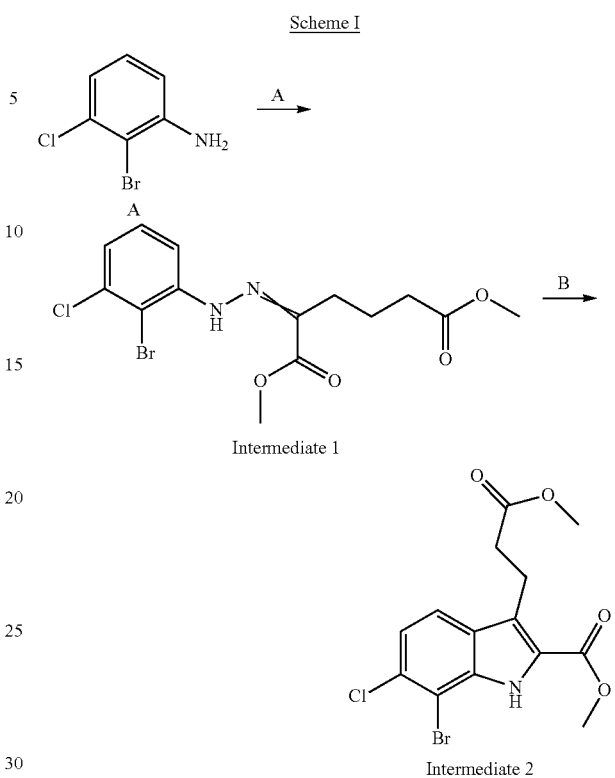

Intermediate 1

Intermediate 2

A = i) $NaNO_2$, aq HCl; ii) methyl 2-oxocyclopentane-1-carboxylate, aq KOAc; iii) $H_2SO_4$, MeOH
B = $H_2SO_4$, MeOH Scheme II

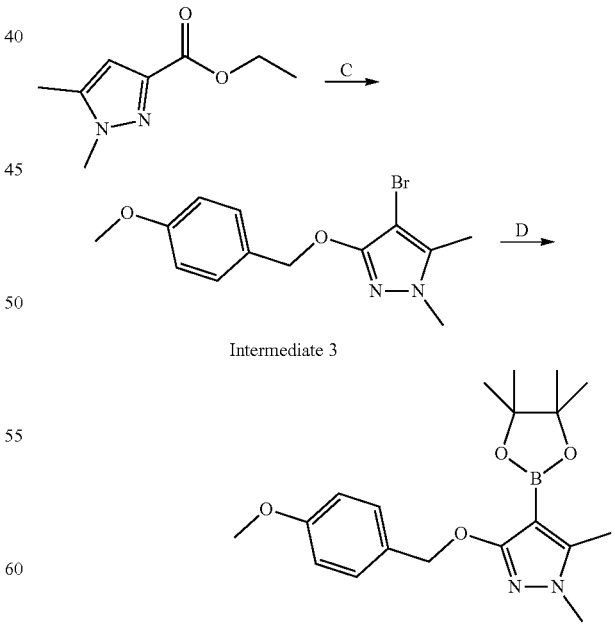

Intermediate 3

Intermediate 4

C = i) $LiAlH_4$, THF; ii) NBS iii) PMBCl, KOH, $Bu_4NHSO_4$, THF
D = i) n-BuLi, THF; ii) i-PrOBPin

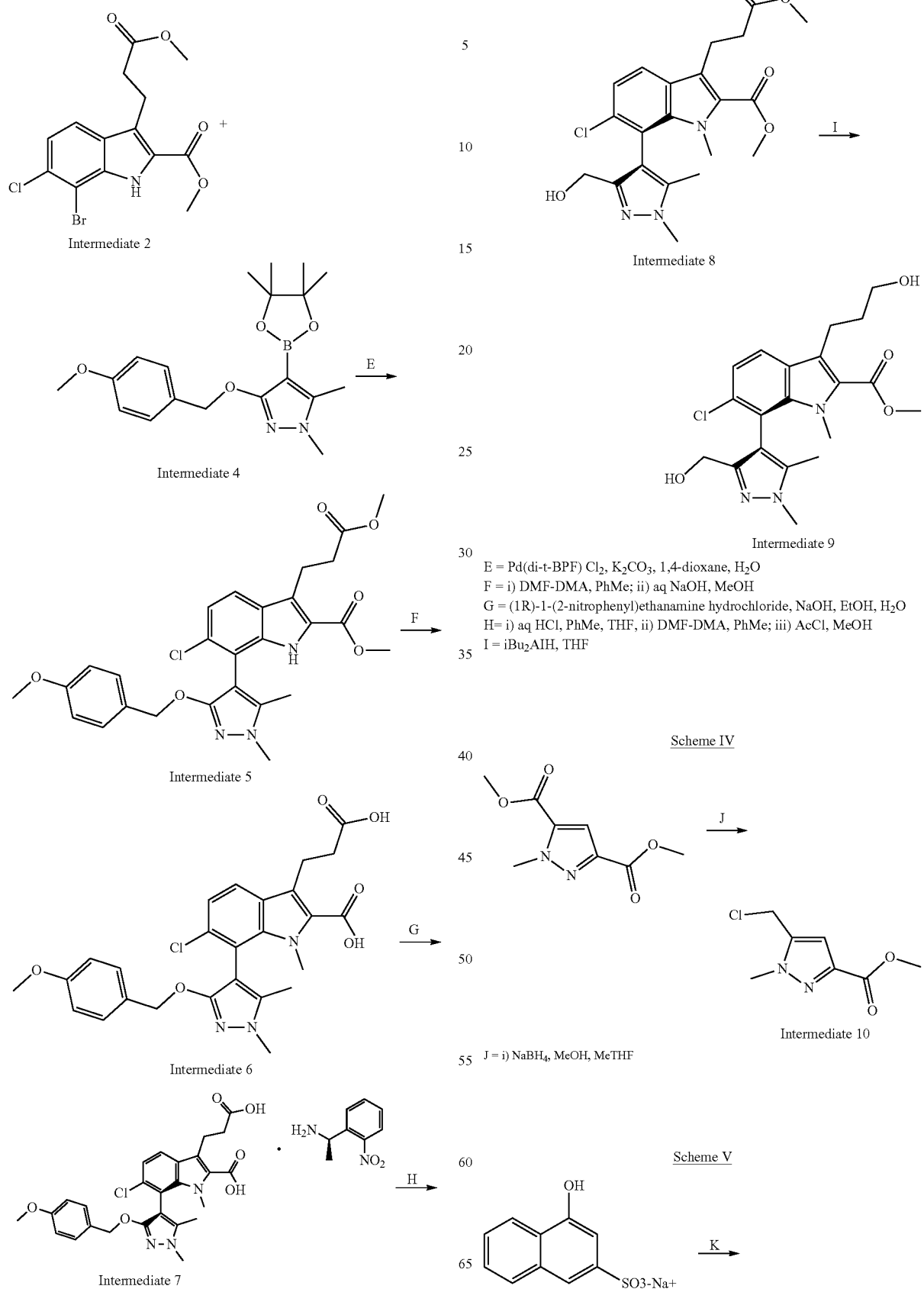

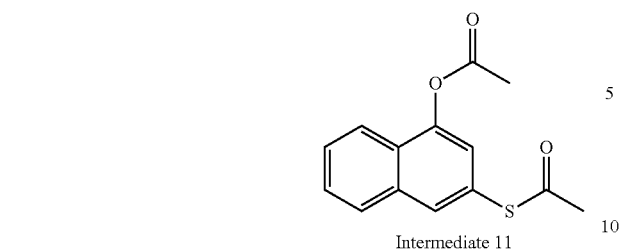
Intermediate 11
K = i) PPh₃, I₂, MeCN; ii) Ac2O, Et3N, DMAP
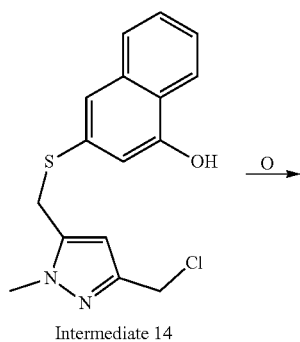
Intermediate 14
Scheme VI
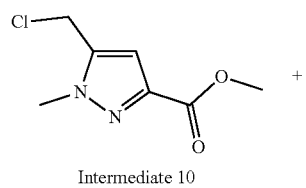
Intermediate 10
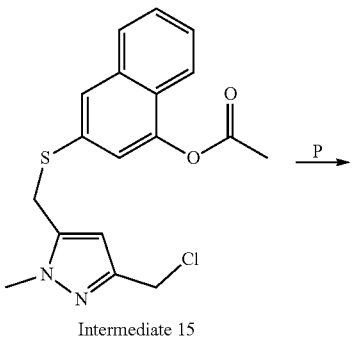
Intermediate 15
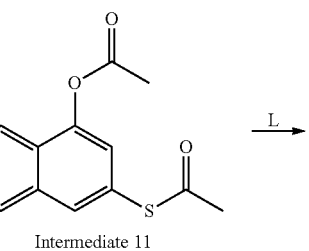
Intermediate 11
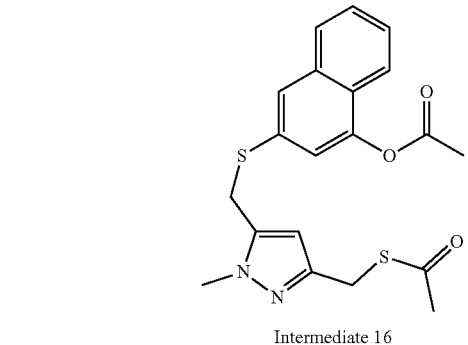
Intermediate 16
L = K₂CO₃, MeOH
M = i-Bu₂AlH, THF
N = MeSO₂Cl, LiCl, DMF
O = Ac2O, DMAP, MeCN
P = KSAc, MeCN
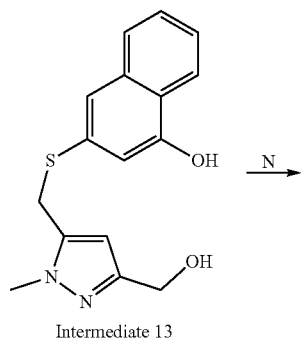
Intermediate 12
Scheme VII
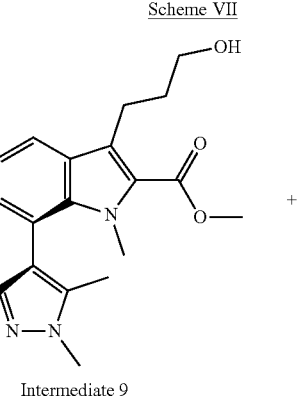
Intermediate 9

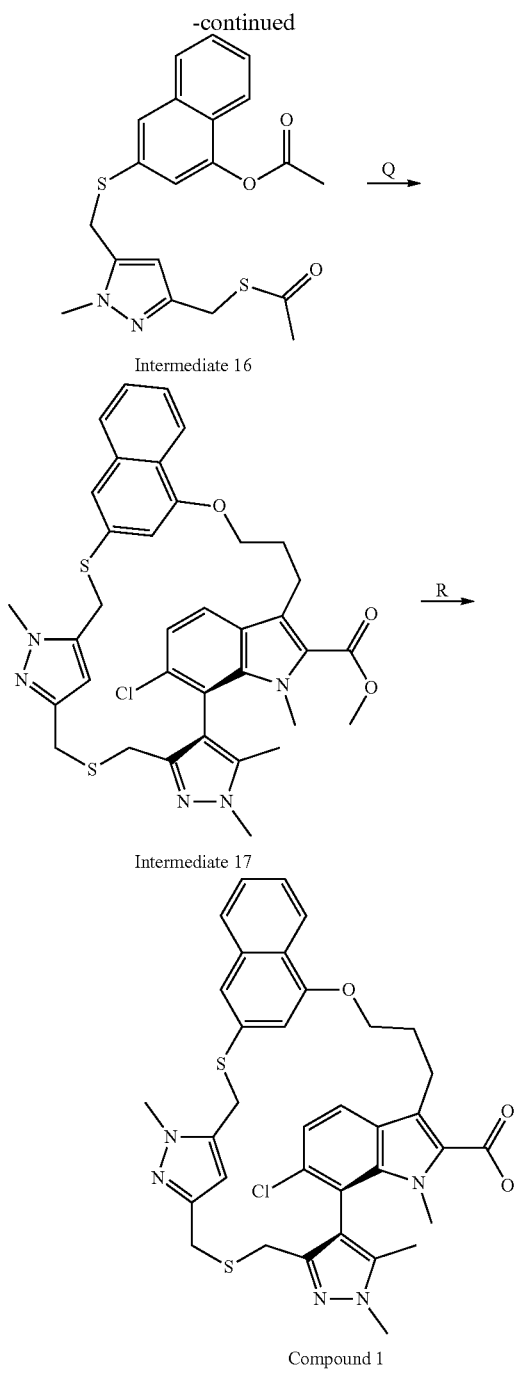

Q = i) intermediate 9, (MeSO₂)₂O, i-Pr₂NEt; ii) LiI, MeCN; iii) in separate vessel, Intermediate 16, NaOMe, MeOH; iv) solution from iii) added to compound from ii) in MeCN; v) addition into hot DMSO
R = NaOH, DMSO, EtOH, H₂O

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilizing Genevac equipment or Biotage v10 evaporator under reduced pressure;

(iii) silica gel chromatography purifications were performed on an automated Novasep Hipersep® or Teledyne Isco CombiFlash® Rf or Teledyne Isco CombiFlash® Companion® system packed using Kromasil® 60-10-SIL silica (10 μm particles, 60 Å pore size) or using prepacked RediSep Rf Gold™ Silica Columns (20-40 μm, spherical particles), GraceResolv™ Cartridges (Davisil® silica) or Silicycle cartridges (40-63 μm).

(iv) chiral analytical chromatography was performed on a Waters X5 SFC-MS with UV detection or a Waters UPC2 SFC-MS with UV and ELSD detection or an Agilent 1100 HPLC system with UV detection.

(v) yields, where present, are not necessarily the maximum attainable;

(vi) in general, the structures of isolated compounds were confirmed by NMR spectroscopy; NMR chemical shift values were measured on the delta scale, using the solvent residual peak as the internal standard [proton magnetic resonance spectra were determined using a Bruker Ultrashield Avance III 500 MHz spectrometer fitted with a QCI cryoprobe, Bruker Ultrashield Avance III 400 MHz spectrometer fitted with a BBFO probe, Bruker Avance 500 (500 MHz), Bruker Avance 400 (400 MHz), Bruker Avance 300 (300 MHz) or Bruker DRX (300 MHz) instrument]; measurements were taken at 27° C. unless otherwise specified; the following abbreviations have been used: s, singlet; d, doublet; t, triplet; q, quartet; m, multiplet; dd, doublet of doublets; ddd, doublet of doublet of doublet; bs, broad signal.

(vii) in general, isolated compounds were also characterized by mass spectroscopy following liquid chromatography using a Waters UPLC fitted with a Waters SQ or QDa mass spectrometer (Column temp 30° C. or 40° C., UV=220-300 nm or 210-400 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 μm, 2.1×50 mm or 2.1×30 mm), or a Waters Acquity BEH C18 (1.7 μm, 2.1×50 mm or 2.1×30 mm), for mid-pH analysis, a Waters Acquity BEH C18 (1.7 μm, 2.1×50 mm) column was used and for basic analysis the column used was a Waters Acquity BEH C18 (1.7 μm, 2.1×50 mm or 2.1×30 mm). Alternatively, a solvent gradient of 2 to 98% B over 1.5 min (total run time with equilibration back to starting conditions 2 min) was used, where A=0.1% formic acid in water and B=0.1% formic acid in acetonitrile (for acidic work) or A=0.1% ammonium hydroxide in water and B=acetonitrile (for basic work). Alternatively a solvent gradient of 92% A+5% B+3% C to 7% A+90% B+3% C or 90% A+5% B+5% D to 5% A+90% B+5% D over 3.6 min (total cycle time with equilibration back to starting conditions, etc., 5.1 min) was used, where A=water, B=acetonitrile, C=1% TFA in water and D=250 mM ammonium acetate in water; The reported molecular ion corresponds to the [M+H]+ unless otherwise specified;

for molecules with multiple isotopic patterns (Br, C, etc.) the reported value is the one obtained with highest intensity unless otherwise specified.

(viii) in general, the wt % purity of compounds were determined against a suitable internal reference standard (for example 1,2,4,5-tetrachloro-3-nitrobenzene, maleic acid or benzyl benzoate) by proton NMR under quantitative conditions.

(ix) large scale reactions were carried out in reactors fitted with heat transfer jackets and serviced with appropriate ancillary equipment; and (x) the following abbreviations have been used:
MeCN acetonitrile
aq. aqueous
conc. concentrated
DCM dichloromethane
di-t-BPF 1,1'-bis(di-tert-butylphosphino)ferrocene
DIBAH diisobutylaluminium hydride
DMAP 4-dimethylaminopyridine
DMF N,N-dimethylformamide
DMF-DMA N,N-dimethylformamide dimethyl acetal
DMSO dimethylsulfoxide
e.e. enantiomeric excess
ES electrospray mode
HPLC high performance liquid chromatography
IPA Isopropyl alcohol
LAH lithium aluminum hydride
MS mass spectrometry
MTBE methyl tert-butyl ether
NBS N-bromosuccinimide
NMR nuclear magnetic resonance
PMB 4-methoxybenzyl
TFA trifluoroacetic acid
THF tetrahydrofuran
UPLC ultra-high performance liquid chromatography
wt % weight percent Intermediate 1: (E/Z)-dimethyl 2-(2-(2-bromo-3-chlorophenyl)hydrazono)hexanedioate

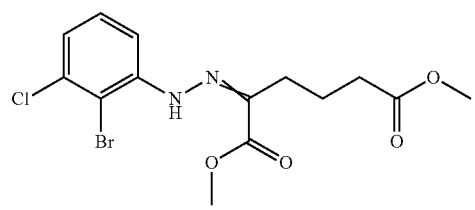 [SMILES: COC(=O)CCCC(=NNc1cccc(Cl)c1Br)C(=O)OC]

A mixture of 2-bromo-3-chloroaniline (2.00 kg, 9.69 mol), hydrochloric acid (36 wt %, 4.85 L, 58.1 mol) and water (5 L) was stirred for 1 h. The resulting solution was cooled to 0° C., then a solution of $NaNO_2$ (702 g, 10.2 mol) in water (2.4 L) was gradually added over 1 h at 0-5° C.

After stirring for 1 h, methyl 2-oxocyclopentane-1-carboxylate (1.38 kg, 9.69 mol) was gradually added at 0-5° C. Then a solution of KOAc (13.3 kg, 136 mol) in water (20 L) was added gradually. The resulting solution was allowed to react for an additional 45 min at 0-5° C. The solution was then extracted three times with DCM (12 L per extraction). The combined organic extracts were washed with brine (10 L) and then charged to another reactor containing a solution of conc. sulfuric acid (4.75 kg, 48.5 mol) in MeOH (3.1 kg). The resulting solution was allowed to react for 3 h at 10-20° C. The solution was concentrated to about 8 L and then two cycles of adding MeOH (18 L per cycle) and distilling off solvent (18 L per cycle) under reduced pressure were completed. The resulting slurry was cooled to 0-10° C., stirred for 1 h and then filtered. The solid was washed with MeOH (2×2 L) and then dried in an oven under reduced pressure to give (E/Z)-dimethyl 2-(2-(2-bromo-3-chlorophenyl)hydrazono)hexanedioate, (Intermediate 1, 3.3 kg, 94 wt %, 82%); m/z (ES+), $[M+H]^+=391$. $^1$H NMR (500 MHz, CHLOROFORM-d, 27° C.) δ 1.98 (m, 2H), 2.41 (t, 2H), 2.59 (t, 2H), 3.66 (s, 3H), 3.87 (s, 3H), 7.05 (dd, 1H), 7.17-7.23 (m, 1H), 7.49 (dd, 1H), 12.48 (bs, 1H).

Intermediate 2: Methyl 7-bromo-6-chloro-3-(3-methoxy-3-oxopropyl)-1H-indole-2-carboxylate

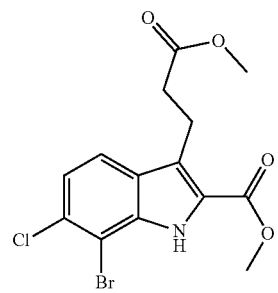 [SMILES: COC(=O)CCc1c(C(=O)OC)[nH]c2c(Br)c(Cl)ccc12]

A solution of (E/Z)-dimethyl 2-(2-(2-bromo-3-chlorophenyl)hydrazono)hexanedioate (Intermediate 1, 3.3 kg, 93.7 wt %, 7.9 mol) in conc. sulfuric acid (8.4 kg, 84 mol) and MeOH (26 L) was stirred for 72 h at 80° C. The reaction mixture was cooled to 0° C. The resulting solids were collected by filtration, washed with MeOH (2 L) and then dried in a vacuum oven at 40° C. to give 2.5 kg of solid. The solid was combined with another 3 batches prepared in the same way at approximately the same scale, to give a total of 11.9 kg of unpurified product, derived from 13.6 kg (93.7 wt %, 32.5 mol) of the starting material.

Half of the unpurified product was added into stirring MeOH (36 L). The mixture was heated to 65° C. and the resulting solution was held at 65° C. for 1 h before cooling to 0° C. The resulting slurry was stirred at 0° C. for 1 h then filtered. The filter cake was washed with MeOH (3 L) and dried in a vacuum oven at 40° C. This was repeated with the remaining material and the materials were combined to give 9.7 kg of solid. 3.7 kg of this was mixed with active charcoal (0.74 kg), DCM (3.4 L) and MeOH (34 L) and the slurry was heated to 65-70° C. for 1 h. The slurry was cooled to 55° C. and filtered. The filter cake was washed with DCM (10 L) and then the combined filtrates were concentrated to about 8 L by distilling off solvent under vacuum. Two cycles of adding MeOH (10 L) and distilling off solvent (10 L) under vacuum were completed and then the resulting slurry was combined with other similarly prepared slurries from the remaining solid. The combined slurry was cooled to 0° C. and stirred for 1 h before filtering. The filter cake was washed with MeOH (3 L) and dried in a 40° C. vacuum oven to yield methyl 7-bromo-6-chloro-3-(3-methoxy-3-oxopropyl)-1H-indole-2-carboxylate (Intermediate 2, 9.4 kg, 97.7 wt %, 76%); m/z (ES+), $[M+H]^+=374$. $^1$H NMR (500 MHz, DMSO-$d_6$, 27° C.), δ 2.60 (t, 2H), 3.26 (t, 2H), 3.53 (s, 3H), 3.89 (s, 3H), 7.28 (d, 1H), 7.73 (d, 1H), 11.62 (bs, 1H).

Intermediate 3: 4-Bromo-3-(((4-methoxybenzyl)oxy)methyl)-1,5-dimethyl-1H-pyrazole

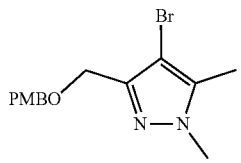

LAH (1.05 M in THF, 15.0 kg, 17.4 mol) was gradually added to a stirring solution of ethyl 1,5-dimethyl-1H-pyrazole-3-carboxylate (5.33 kg, 31.7 mol) in THF (10.7 L) over 1.5 h at 4-23° C., followed by THF (1.0 L). After 30 min, the solution was cooled to 15° C., then, while continuing to cool, a solution of water (0.66 L, 37 mol) in THF (1.9 L) was gradually added over 20 min. Aq. NaOH (15 wt %, 0.66 L, 2.8 mol) was then added over a few min, followed by water (2.0 L). The resulting slurry was stirred for 20 min at 4-11° C. then filtered under suction. The collected solids were washed four times with THF (10.7 L per wash) to give (1,5-dimethyl-1H-pyrazol-3-yl)methanol as a solution in the collected filtrates.

The reactor was rinsed with 1M HCl, water and THF before charging the filtrates back in. Three portions of NBS (1.82 kg per portion, 99.4 wt %, 30.6 mol in total) were charged to the solution, stirring for 7-8 min at 19-27° C. between portions and then for 45 min afterwards at 21-28° C. A solution prepared from Na$_2$SO$_3$ (0.81 kg, 99 wt %, 6.4 mol), NaOH (50 wt % in water, 4.6 kg, 57 mol) and water (16 L) was then added and the resulting mixture stirred for 10 min at 25-26° C. The layers were separated and the lower layer was washed with THF (16 L). The upper layers were combined and evaporated to dryness to give (4-bromo-1,5-dimethyl-1H-pyrazol-3-yl)methanol as a solid.

This unpurified (4-bromo-1,5-dimethyl-1H-pyrazol-3-yl)methanol was re-dissolved in THF (18.8 L) and heated with stirring to 50° C., then tetrabutylammonium bisulfate (0.32 kg, 0.95 mol), 1-(chloromethyl)-4-methoxybenzene (5.4 L, 97.6 wt %, 40 mol) and a THF (2.8 L) line wash were added. KOH (45 wt % in water, 13.7 L, 159 mol) was added gradually over 45 min to the vigorously stirring mixture at 47-57° C., before continuing to stir for 4 h at 55-50° C. The mixture was then cooled to 20° C. and held with stirring for 63 h. The mixture was re-heated to 50° C., water (18.7 L) was added and the mixture was stirred for 10 min. The lower layer was removed and the solution remaining in the reactor was cooled to 20° C. 4-Bromo-3-(((4-methoxybenzyl)oxy)methyl)-1,5-dimethyl-1H-pyrazole (0.01 kg, 0.03 mol) was added as crystallization seed followed by heptane (32 L), gradually over 45 min, during which time crystallization started. The slurry was held with stirring for 30 min at 20° C. before gradually charging more heptane (22 L) over 45 min and cooling to 0° C. After 17 h, more heptane (11 L) was added. After a further 1 h at 0° C., the slurry was filtered under suction. The filter cake was washed with a cooled (0° C.) mixture of heptane (17 L) and THF (4.3 L) and then dried in a 40° C. vacuum oven to give 4-bromo-3-(((4-methoxybenzyl)oxy)methyl)-1,5-dimethyl-1H-pyrazole (Intermediate 3, 8.78 kg, 96 wt %, 82%); m/z (ES+), [M+H]$^+$=325. $^1$H NMR (500 MHz, DMSO-d$_6$, 27° C.) δ 2.22 (s, 3H), 3.74 (s, 3H), 3.75 (s, 3H), 4.32 (s, 2H), 4.39 (s, 2H), 6.87-6.93 (m, 2H), 7.22-7.27 (m, 2H).

Intermediate 4: 3-(((4-Methoxybenzyl)oxy)methyl)-1,5-dimethyl-4-(4,4,5,5-tetramethyl-1,3,2-dioxaborolan-2-yl)-1H-pyrazole

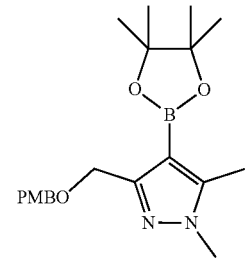

Butyllithium (15 wt % in hexane, 7.27 kg, 17.3 mol) was gradually added to a stirred slurry of 4-bromo-3-(((4-methoxybenzyl)oxy)methyl)-1,5-dimethyl-1H-pyrazole (Intermediate 3, 5.27 kg, 96 wt %, 15.6 mol) in THF (43 L) at −73° C. to −66° C. over 1.5 h. The resulting solution was agitated for 1.7 h at −77° C. to −66° C., then 2-isopropoxy-4,4,5,5-tetramethyl-1,3,2-dioxaborolane (3.4 L, 16 mol), followed by a THF (3.0 L) line wash, was added over 15 min. The solution was agitated for 1.5 h at −77° C. to −63° C., then a solution of acetic acid (0.89 L, 16 mol) in toluene (25.3 L) was gradually added over 15 min at −77° C. to −58° C. The mixture was then warmed to 20° C. before heating and distilling off solvent (48 L) at 67-82° C. (atmospheric pressure). The mixture was cooled to 65° C., water (25.5 L) was added and the mixture was stirred for 10 min. The lower layer was removed and then more solvent (25.4 L) was distilled off at 72-119° C. (atmospheric pressure; final vapor temperature 108° C.). The resulting solution was cooled to 40° C. and diluted with heptane (50.6 L) over 10 min, during which time the mixture was cooled to 21° C. and spontaneous crystallization began. 3-(((4-Methoxybenzyl)oxy)methyl)-1,5-dimethyl-4-(4,4,5,5-tetramethyl-1,3,2-dioxaborolan-2-yl)-1H-pyrazole (29 g) was then added as seed nevertheless. The slurry was agitated at approximately 21° C. for 0.6 h, cooled to approximately −5° C. over 1.5 h, then held overnight (18 h) at that temperature. The slurry was filtered under suction and then the filter cake was washed with cold (−0° C.) heptane before drying in a 40° C. vacuum oven to give 3-(((4-methoxybenzyl)oxy)methyl)-1,5-dimethyl-4-(4,4,5,5-tetramethyl-1,3,2-dioxaborolan-2-yl)-1H-pyrazole (Intermediate 4, 4.50 kg, 99 wt %, 77%); m/z (ES+), [M+H]$^+$=373. $^1$H NMR (500 MHz, DMSO-d$_6$, 27° C.) δ 1.23 (s, 12H), 2.34 (s, 3H), 3.68 (s, 3H), 3.73 (s, 3H), 4.40 (s, 2H), 4.42 (s, 2H), 6.85-6.91 (m, 2H), 7.20-7.25 (m, 2H).

Intermediate 5: (±)-Methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate

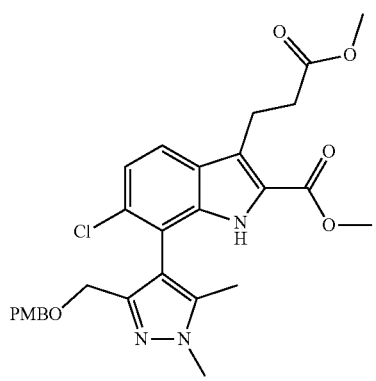

3-(((4-Methoxybenzyl)oxy)methyl)-1,5-dimethyl-4-(4,4,5,5-tetramethyl-1,3,2-dioxaborolan-2-yl)-1H-pyrazole (Intermediate 4, 3.30 kg, 99 wt %, 8.78 mol), methyl 7-bromo-6-chloro-3-(3-methoxy-3-oxopropyl)-1H-indole-2-carboxylate (Intermediate 2, 3.20 kg, 97.7 wt %, 8.35 mol), $K_2CO_3$ (1.60 kg, 11.6 mol) and 1,1'-bis(di-tert-butylphosphino)ferrocene palladium dichloride (0.132 kg, 0.203 mol) were charged to a 100 L reactor under nitrogen. The reactor headspace was then evacuated and re-filled with nitrogen three times. 1,4-Dioxane (26.3 L) and water (3.3 L) were sparged with nitrogen under reduced pressure for 5-10 min before they were sequentially added and the resulting slurry was heated at 80° C. with stirring for 5 h. The reaction mixture was cooled to 20° C. and held overnight (16 h) before diluting with MTBE (33 L) and water (33 L). N-Acetyl cysteine (0.165 kg, 1.01 mol) was added and the mixture was stirred for 15 min. The lower layer, once settled, was removed. The upper layer was then washed sequentially with hydrochloric acid (37 wt %, 2.7 L, 33 mol) in water (30 L) and then water (32 L) to give a MTBE solution of (±)-methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate (Intermediate 5, 22.9 kg, 19.1 wt %, 97%).

Intermediate 6: (±)-3-(2-Carboxyethyl)-6-chloro-7-(3-(((4-methoxybenzyl)oxy)methyl)-1,5-dimethyl-1H-pyrazol-4-yl)-1-methyl-1H-indole-2-carboxylic Acid

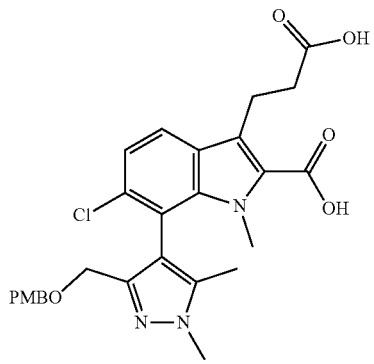

A MTBE solution of (±)-methyl 6-chloro-3-(3-methoxy-3-oxopropyl)-7-(3-(((4-methoxybenzyl)oxy)methyl)-1,5-dimethyl-1H-pyrazol-4-yl)-1H-indole-2-carboxylate (Intermediate 5, 22.94 kg, 19.1 wt %, 8.12 mol) was agitated with a mercaptopropyl functionalized silica-based palladium scavenger (Quadrasil™ MP, 1.1 kg) and toluene (44 L) at 20° C. for 1 h. The slurry was filtered and the waste solids were washed with toluene (13 L). The combined filtrates were concentrated by distilling off solvent (44 L) at 75-107° C. DMF-DMA (5.5 L, 41 mol) was then added at 91° C. The solution was heated to reflux, held for 22 h at approximately 108° C., during which four portions of solvent (2, 4.5, 4.5 and 4.4 L) were distilled off (immediately after reaching reflux, then after 2.0, 3.4 and 4.8 h), and then cooled to 55° C. NaCl (2.2 kg) solution in water (20 L) was charged, then the resulting biphasic mixture was removed from the vessel and filtered back in through a 5 µm in-line filter. The screened mixture was agitated at 50-53° C. for 10 min and then, once settled, the lower layer was removed. MeOH (22 L) and a solution of aq. NaOH (3.3 kg, 50 wt %, 41 mol) in water (18 L) were then added and the resulting biphasic mixture was agitated at 55° C. for 3 h. After settling, the layers were removed to separate containers. The lower layer (containing the product) was then returned to the reactor and agitated at 55° C. Acetic acid (4.6 kg, 77 mol) solution in water (4.4 L) was then gradually added over 25 min, followed by a 3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid (0.02 kg, 0.04 mol) crystallization seed. The mixture was held at 49-56° C. for 2 h, cooled to 20° C. over 2 h and then held at 20° C. for 13 h. The resulting slurry was filtered under suction. Water (11 L) was used to rinse the reactor and filter cake, which was then partly dried on the filter by continuing suction for 6 h at ambient temperature and completely dried in a 40° C. vacuum oven to give (±)-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid (Intermediate 6, 3.78 kg, 99.0 wt %, 86%); m/z (ES+), $[M+H]^+$=526. $^1H$ NMR (500 MHz, DMSO-$d_6$, 27° C.) δ 2.01 (s, 3H), 2.50-2.57 (m, 2H), 3.18-3.29 (m, 2H), 3.40 (s, 3H), 3.68 (s, 3H), 3.82 (s, 3H), 4.08 (d, 1H), 4.14 (d, 1H), 4.19 (d, 1H), 4.21 (d, 1H), 6.64-6.69 (m, 2H), 6.69-6.74 (m, 2H), 7.25 (d, 1H), 7.75 (d, 1H), 12.71 (bs, 1H).

Intermediate 7: ($R_a$)-3-(2-Carboxyethyl)-6-chloro-7-(3-(((4-methoxybenzyl)oxy)methyl)-1,5-dimethyl-1H-pyrazol-4-yl)-1-methyl-1H-indole-2-carboxylic acid-(1R)-1-(2-nitrophenyl)ethanamine (1:1 Salt)

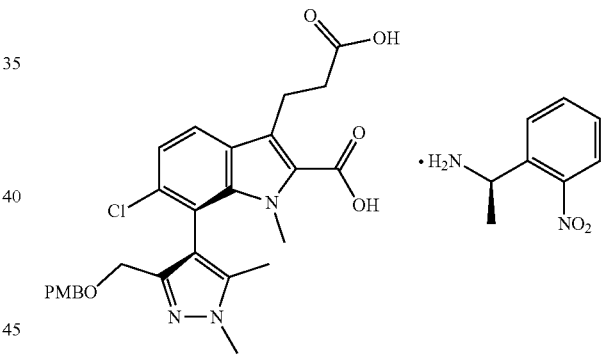

NaOH (50 wt % in water, 0.95 L, 18 mol), followed by an ethanol (1.8 L) rinse, was added to a stirring slurry of (±)-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid (Intermediate 6, 9.38 kg, 97.5 wt %, 17.4 mol) and (1R)-1-(2-nitrophenyl)ethanamine hydrochloride (2.48 kg, 91 wt %, 11.1 mol) in water (7.4 kg) and ethanol (64 L) at 20° C. While heating the resulting solution to 78° C., spontaneous crystallization of the product started (at or below 41° C.). After heating to 78° C., three cycles of cooling the slurry to 63° C. over 1.3 h, heating back to 78° C. over 0.6 h and holding for 10 min were completed. The slurry was then cooled, to 63° C. over 1.2 h, then to 20° C. over 1.6 h, before holding at 20° C. overnight and then filtering under suction. Ethanol (18 L) was used to rinse the reactor and filter cake. Once well de-liquored, the filter cake was returned to the reactor. (This solid typically has approximately 92% e.e. of the desired di-acid). Water (7.3 L) and ethanol (66 L) were charged and the reactor contents were heated with stirring to 78° C. The resulting slurry was cooled to 63° C. over 1.3 h, then to 20° C. over 1.6 h, before holding at 20° C. overnight and then filtering under suction. Ethanol (18 L) was used to rinse the reactor and filter cake. The filter cake was dried in a 40° C. vacuum oven to give ($R_a$)-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid-(1R)-1-(2-nitrophenyl)ethanamine (1:1 salt) (Intermediate 7, 5.23 kg, 97.5 wt %, 99.0% e.e., 7.36 mol) in 42.3% yield; m/z (ES+), [M+H]$^+$=526 (acid), 167 (amine). $^1$H NMR (500 MHz, DMSO-$d_6$, 27° C.) δ 1.49 (d, 3H), 2.00 (s, 3H), 2.61 (t, 2H), 3.10-3.22 (m, 2H), 3.38 (s, 3H), 3.68 (s, 3H), 4.11 (d, 1H), 4.14 (d, 1H), 4.17 (d, 1H), 4.22 (d, 1H), 4.66 (q, 1H), 6.67-6.72 (m, 2H), 6.75-6.80 (m, 2H), 7.18 (d, 1H), 7.54-7.60 (m, 1H), 7.63 (d, 1H), 7.76-7.82 (m, 1H), 7.90-7.94 (m, 1H), 7.93-7.97 (m, 1H), 9.16 (bs, 3H).

Chiral purity analysis HPLC method details: column=Chiralpak AD-H (4.6×250 mm, 5 μm); temperature=25° C.; mobile phase=70:30 hexane:ethanol by volume containing 0.2% TFA, flowing at 1.0 mL/min; detection by UV at 254 nm; inj. volume=10 μL (this may be adjusted to achieve a suitable limit of detection); retention times 4.8 and 13.7 min for the $R_a$ and $S_a$ enantiomers respectively.

Intermediate 8: ($R_a$)-Methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate

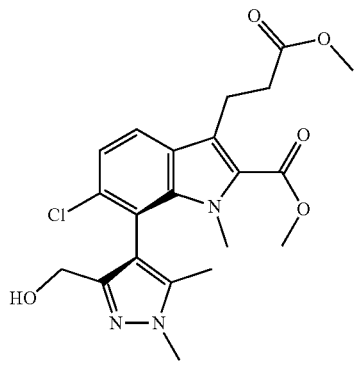

Hydrochloric acid (37 wt %, 0.77 L, 9.2 mol) was added to a stirring slurry of ($R_a$)-3-(2-carboxyethyl)-6-chloro-7-(3-(((4-methoxybenzyl)oxy)methyl)-1,5-dimethyl-1H-pyrazol-4-yl)-1-methyl-1H-indole-2-carboxylic acid-(1R)-1-(2-nitrophenyl)ethanamine (1:1 salt) (Intermediate 7, 5.23 kg, 97.5 wt %, 7.36 mol) in THF (20.5 L) and water (20.5 L) at 45° C. After 5 min, toluene (41 L) was added and the mixture was stirred for 10 min. The lower layer was removed and the upper layer was diluted with toluene (20.5 L) and concentrated by distilling off solvent (60 L) under reduced pressure (590 mbar) at 48-92° C. DMF-DMA (3.45 L, 25.8 mol) was added to the resulting mixture at 90° C., giving a solution, which was heated to reflux, held at reflux (98° C.) for 8 h, then cooled to and held at 49° C. for 16 h. DMF-DMA (1.0 L, 7.5 mol) was added and the mixture was refluxed at 100° C. for an additional 3.6 h before cooling to 50° C. Water (12.7 L) was added and the mixture was stirred for 15 min. The lower layer was removed. MeOH (20 L) was added to the upper layer, followed by a 10 min gradual addition of acetyl chloride (2.15 L, 29.9 mol) to the stirred solution. The solution was heated at 60° C. for 21 h then transferred to containers. Toluene (10 L) and $K_2CO_3$ (2.56 kg, 18.4 mol) in water (20.5 L) were charged to the empty reactor and the mixture was heated to 55° C. The completed reaction solution was then gradually added back into the reactor over 20 min, followed by a toluene (10 L) rinse. Stirring was stopped after a further 10 min at 55° C. and once settled, the lower layer was removed. The upper layer was concentrated by distilling off solvent (21 L) under reduced pressure (540 mbar) at 55-93° C. The solution was diluted with heptane (10 L) at 50° C. and then seeded with ($R_a$)-methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (16 g, 0.037 mol). After allowing the crystallisation to establish for 1 h at 50° C., more heptane (20 L) was gradually added over 1 h. The slurry was then cooled to 20° C. over 2 h and stirred for 65 h before it was filtered under suction. The filter cake was washed with heptane (10 L) and then dried in a 40° C. vacuum oven to give ($R_a$)-methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (Intermediate 8, 2.85 kg, 98 wt %, 87%); m/z (ES+), [M+H]$^+$=434. $^1$H NMR (500 MHz, DMSO-$d_6$, 27° C.) δ 1.95 (s, 3H), 2.57-2.64 (m, 2H), 3.17-3.33 (m, 2H), 3.44 (s, 3H), 3.57 (s, 3H), 3.79 (s, 3H), 3.84 (s, 3H), 4.13 (dd, 1H), 4.23 (dd, 1H), 4.72 (dd, 1H), 7.26 (d, 1H), 7.72 (d, 1H).

Intermediate 9: ($R_a$)-Methyl 6-chloro-7-(3-(hydroxymethyl)-1,5-dimethyl-1H-pyrazol-4-yl)-3-(3-hydroxypropyl)-1-methyl-1H-indole-2-carboxylate

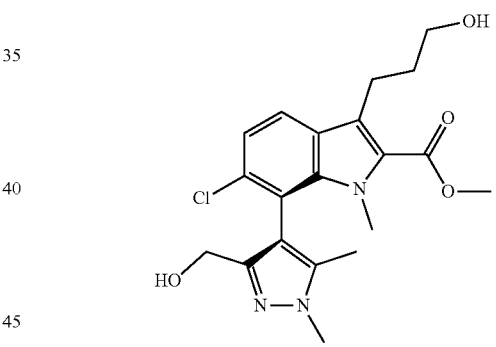

($R_a$)-Methyl 6-chloro-7-(3-(hydroxymethyl)-1,5-dimethyl-1H-pyrazol-4-yl)-3-(3-methoxy-3-oxopropyl)-1-methyl-1H-indole-2-carboxylate (Intermediate 8, 2.25 kg, 98 wt %, 5.08 mol) was dissolved in THF (13.3 L) and the resulting solution was cooled to −45° C. DIBAH (20.3 wt % in hexane; 11.0 kg, 15.7 mol) was then added over 1.1 h at or below −41° C. The reaction mixture was held at approximately −45° C. for a further 4.4 h, during which time three further portions of DIBAH (20.3 wt % in hexane; 1.32, 0.25 and 0.07 kg; 1.88, 0.36 and 0.10 mol) were added after 1.4, 2.8 and 3.7 h. IPA (2.2 L, 29 mol) was then added to the reaction mixture, before heating to 20° C. over 2 h and holding at that temperature for 2.5 h.

Meanwhile, in another reactor, sodium potassium tartrate tetrahydrate (6.47 kg, 22.9 mol) and water (22 L) were charged. After a few minutes of agitation at 20° C., a solution was formed and then isopropyl acetate (22 L) was added. The resulting biphasic mixture was heated to 50° C.

The ester reduction reaction mixture was transferred to the vigorously stirred aqueous tartrate and isopropyl acetate mixture at 50° C. over 20 min, followed by a THF (1.5 L) rinse. Vigorous stirring at 50° C. was continued for 1.9 h. The lower layer was removed. The upper layer was washed with water (4.45 L), then removed and filtered back into the reactor through a 5 μm in-line filter, followed by an isopropyl acetate (1.1 L) line wash. The solution was concentrated by distilling off solvent (32 L) at 58-74° C. (atmospheric pressure) then cooled to 20° C. The solution was transferred to a smaller vessel, followed by an isopropyl acetate (1.1 L) line wash, and then further concentrated (to approximately 9 L) by distilling off more solvent (15 L) at 73-85° C. (atmospheric pressure). The stirring solution was then cooled to 70° C., seeded with ($R_a$)-methyl 6-chloro-7-(3-(hydroxymethyl)-1,5-dimethyl-1H-pyrazol-4-yl)-3-(3-hydroxypropyl)-1-methyl-1H-indole-2-carboxylate (2 g, 97.9 wt %, 5 mmol), cooled to 20° C. over 1 h and held at 20° C. for 24 h. The resulting slurry was filtered under suction. The filter cake was washed with isopropyl acetate (2.2 L) and then dried in a 40° C. vacuum oven to give ($R_a$)-methyl 6-chloro-7-(3-(hydroxymethyl)-1,5-dimethyl-1H-pyrazol-4-yl)-3-(3-hydroxypropyl)-1-methyl-1H-indole-2-carboxylate (Intermediate 9, 1.76 kg, 98.0 wt %, 84%); m/z (ES+), [M+H]$^+$=406. $^1$H NMR (500 MHz, DMSO-$d_6$, 27° C.) δ 1.68-1.77 (m, 2H), 1.96 (s, 3H), 2.93-3.05 (m, 2H), 3.43 (s, 3H), 3.42-3.48 (m, 2H), 3.80 (s, 3H), 3.84 (s, 3H), 4.14 (dd, 1H), 4.23 (dd, 1H), 4.48 (t, 1H), 4.71 (dd, 1H), 7.25 (d, 1H), 7.71 (d, 1H).

Intermediate 10: Methyl 5-(chloromethyl)-1-methyl-1H-pyrazole-3-carboxylate

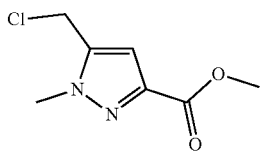

Sodium carbonate (2.14 kg, 20.2 mol) was added to a stirring solution of dimethyl 1-methyl-1H-pyrazole-3,5-dicarboxylate (7.95 kg, 40.1 mol) in MeOH (80 L) at 20±5° C. The slurry was stirred for 0.5 h and then filtered. The filter cake was washed with 2-methylTHF (16 L) and then the filtrates were returned to the reactor, followed by 2-methylTHF (24 L). The solution was cooled to 15±3° C. and sodium borohydride (3.05 kg, 80.7 mol) was charged in ten portions at 15±3° C. The mixture was stirred for 2 h at 18±3° C. after adding NaBH$_4$. It was then quenched by gradually charging acetone (16.4 kg, 283 mol) at 18±3° C., then stirred for 1 h at 20±5° C. Aq. HCl (37 wt %, ~8.6 Kg, 87 mol) was then slowly added, keeping the temperature below 30° C., to adjust the pH to 2-3, then the mixture was stirred for 1 h. Saturated aq. Na$_2$CO$_3$ (~4 L) was then slowly added to adjust the pH to 5-6, then the mixture was stirred for 3 h. The mixture was filtered and the filter cake was washed with DCM (16 L). The filtrates were concentrated to approximately 20 L by distillation under reduced pressure, not heating above 40° C., then diluted with DCM (40 L) and concentrated again by distilling off solvent (approx. 40 L) under reduced pressure. DCM (80 L) and purified water (32 L) were charged and the resulting mixture was stirred for at least 10 min. The lower (organic) phase was collected and the upper (aqueous) phase was extracted four times with more DCM (40 L per portion). The combined organic phases were concentrated to approximately 20 L by vacuum distillation below 40° C. DCM (80 L) was added and the solution was concentrated again by distilling off solvent (approx. 40 L). The resulting methyl 5-(hydroxymethyl)-1-methyl-1H-pyrazole-3-carboxylate solution was then diluted with DCM (80 L) and cooled to 10±5° C., whereupon thionyl chloride (4.80 kg, 40.4 mol) was gradually added while keeping the temperature below 15° C. The mixture was then stirred for 1 h at 20±5° C. The mixture was concentrated to not more than 20 L by vacuum distillation below 40° C., then DCM (64 L) and purified water (80 L) were added. After phase separation, the lower (organic) phase was washed twice with aq. Na$_2$CO$_3$ (9 wt %, 80 L per portion) and then with purified water (80 L). The washed organic phase was concentrated to approximately 14 L by vacuum distillation below 40° C. Two cycles of slowly adding heptane (40 L) and then vacuum distilling to approximately 24 L at below 45° C. were then completed. More heptane (40 L) was slowly added and the resulting slurry was stirred at 20±5° C. for at least 0.5 h before filtering. The filter cake was washed with heptane (8.0 L) and then dried in a 45° C. vacuum oven to give methyl 5-(chloromethyl)-1-methyl-1H-pyrazole-3-carboxylate (Intermediate 10, 4.87 kg, 64%); m/z (ES+), [M+H]$^+$=189. $^1$H NMR (500 MHz, CDCl$_3$, 27° C.) δ 3.91 (s, 3H), 3.99 (s, 3H), 4.59 (s, 2H), 6.82 (s, 1H).

Intermediate 11: 3-(Acetylthio)naphthalen-1-yl acetate

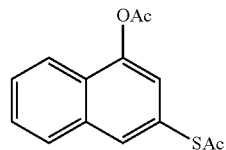

A stirring mixture of MeCN (102 L), sodium 4-hydroxynaphthalene-2-sulfonate (17.00 kg, 69.05 mol), triphenylphosphine (65.1 kg, 248 mol) and iodine (14.0 kg, 55.2 mol) was heated at 80±5° C. for 6 h. The mixture was cooled and stirred at 0±5° C. for at least 2 h. The waste solids were filtered off to give the crude 3-mercaptonaphthalen-1-ol dissolved in the filtrates (also containing a large quantity of triphenylphosphine oxide), which were recharged to the reactor followed by DMAP (0.84 kg, 6.9 mol). Keeping the temperature below 25° C., triethylamine (21.0 kg, 207 mol) and then acetic anhydride (17.6 kg, 173 mol) were gradually added. The mixture was stirred for 2 h at 15-20° C. then distilled under reduced pressure to less than 85 L, not heating above 45° C. DCM (85 L) was added and then the mixture was distilled under reduced pressure to less than 85 L, not heating above 40° C. More DCM (170 L) was added and then the mixture was washed with water (170 L), followed by aq. NaCl (17 wt %, 170 L). The lower organic phase was distilled under reduced pressure to less than 51 L, not heating above 40° C. Then three cycles of diluting the solution with MeOH (85 L) and distilling under reduced pressure to less than 51 L at below 40° C. were completed to give a methanolic solution of crude 3-(acetylthio)naphthalen-1-yl acetate (Intermediate 11, 40.9 kg, 31.3 wt %, 49.2 mol) in 71% yield. The solution, which also contains a large quantity of triphenylphosphine oxide, was used directly in the preparation of Intermediate 12.

Intermediate 12: Methyl 5-(((4-hydroxynaphthalen-2-yl)thio)methyl)-1-methyl-1H-pyrazole-3-carboxylate

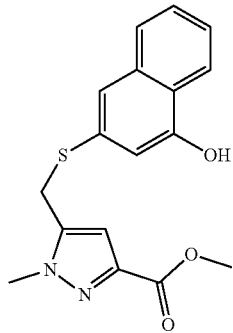

3-(Acetylthio)naphthalen-1-yl acetate (Intermediate 11, 40.9 kg, 31.3 wt % in methanol, 49.2 mol), methanol (64 L) and $K_2CO_3$ (13.6 kg, 98.4 mol) were stirred at 15-20° C. Methyl 5-(chloromethyl)-1-methyl-1H-pyrazole-3-carboxylate (Intermediate 10, 7.40 kg, 39.2 mol) was added portionwise while keeping the temperature below 25° C. The slurry was then stirred for 2 h at 20-25° C. In response to HPLC analysis, four further portions of methyl 5-(chloromethyl)-1-methyl-1H-pyrazole-3-carboxylate (Intermediate 10, 0.46 kg, 2.4 mol per portion) were charged, stirring for 1 h at 20-25° C. after each portion. Purified water (109 L) was gradually added at 15-20° C., the resulting mixture was stirred for at least 2 h, then allowed to settle for at least 3 h. The liquors were removed via tubing, leaving the settled sticky solids in the reactor, to which ethanol (25.5 L) was then added. The mixture was stirred for at least 1 h at 15±5° C. before filtering the slurry obtained. The filter cake was washed with ethanol (6.4 L) then dried in a 45±5° C. vacuum oven to give methyl 5-(((4-hydroxynaphthalen-2-yl)thio)methyl)-1-methyl-1H-pyrazole-3-carboxylate (Intermediate 12, 13.05 kg, 99.3 wt %, 81%); m/z (ES+), [M+H]$^+$=329. $^1$H NMR (500 MHz, DMSO, 27° C.) δ 3.72 (s, 3H), 3.90 (s, 3H), 4.39 (s, 2H), 6.63 (s, 1H), 6.79 (d, 1H), 7.28-7.32 (m, 1H), 7.38 (ddd, 1H), 7.45 (ddd, 1H), 7.72 (d, 1H), 8.07 (d, 1H), 10.55 (bs, 1H).

Intermediate 13: 3-(((3-(Hydroxymethyl)-1-methyl-1H-pyrazol-5-yl)methyl)thio)naphthalen-1-ol

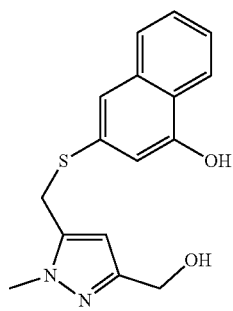 [SMILES: Cn1nc(CO)cc1CSc1cc(O)c2ccccc2c1]

Methyl 5-(((4-hydroxynaphthalen-2-yl)thio)methyl)-1-methyl-1H-pyrazole-3-carboxylate (Intermediate 12, 12.7 kg, 99.3 wt %, 38.4 mol) was dissolved in THF (254 L) at 30±5° C. and then the solution cooled to 15±5° C. DIBAH (1 M in hexane, 155 L, 155 mol) was slowly added while keeping the temperature at 15±5° C. The mixture was then stirred for 0.5 h at 20±5° C., analyzed by HPLC, and then transferred gradually into aqueous hydrochloric acid (4 M, 114 L, 456 mol) at 5-20° C. The biphasic mixture was vacuum distilled at below 40° C. to not more than approximately 120 L. The resulting slurry was cooled to 15±5° C., then filtered. The filter cake was washed with purified water (25 L) and then recharged to the reactor, together with DCM (57 L) and THF (6.4 L). After stirring the mixture for at least 10 h at 20±5° C., it was filtered. The filter cake was washed with DCM (25 L) and then dried in a vacuum oven at 45±5° C. to give 3-(((3-(hydroxymethyl)-1-methyl-1H-pyrazol-5-yl)methyl)thio)naphthalen-1-ol (Intermediate 13, 10.45 kg, 95.5 wt %, 87%); m/z (ES+), [M+H]$^+$=301. $^1$H NMR (500 MHz, DMSO-d$_6$, 27° C.) δ 3.77 (s, 3H), 4.28 (s, 2H), 4.37 (s, 2H), 4.87 (bs, 1H), 6.14 (s, 1H), 6.81 (d, 1H), 7.35 (d, 1H), 7.39 (ddd, 1H), 7.47 (ddd, 1H), 7.72-7.75 (m, 1H), 8.03-8.06 (m, 1H), 10.34 (s, 1H).

Intermediate 14: 3-(((3-(Chloromethyl)-1-methyl-1H-pyrazol-5-yl)methyl)thio)naphthalen-1-ol

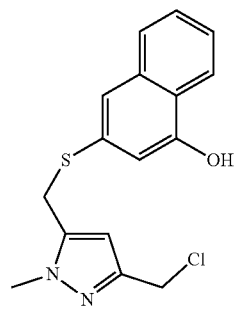 [SMILES: Cn1nc(CCl)cc1CSc1cc(O)c2ccccc2c1]

Methanesulfonyl chloride (6.28 kg, 54.8 mol) was gradually added to a stirring mixture of 3-(((3-(hydroxymethyl)-1-methyl-1H-pyrazol-5-yl)methyl)thio)naphthalen-1-ol (Intermediate 13, 10.30 kg, 95.5 wt %, 32.7 mol), anhydrous lithium chloride (2.91 kg, 68.6 mol) and DMF (51.5 L) while keeping the temperature below 10° C. The mixture was stirred for 2 h at 15-20° C. EtOAc (155 L) was then added, followed by purified water (155 L) and the mixture was mixed well. The lower layer was removed and the upper layer was washed twice with aq. NaCl (17 wt %; 155 L per portion). The upper layer was then vacuum distilled to less than 50 L at below 35° C. Heptane (155 L) was then slowly added at 30±5° C. before cooling the mixture to 0-5° C. After stirring the slurry for at least 1 h, it was filtered. The filter cake was washed with heptane (10.3 L) and then dried in a 30-35° C. vacuum oven to give 3-(((3-(chloromethyl)-1-methyl-1H-pyrazol-5-yl)methyl)thio)naphthalen-1-ol (Intermediate 14, 9.72 kg, 95.3 wt %, 89%); m/z (ES+), [M+H]$^+$=319. $^1$H NMR (500 MHz, CDCl$_3$, 27° C.) δ 3.80 (s, 3H), 4.07 (s, 2H), 4.50 (s, 2H), 6.11 (s, 1H), 6.70 (d, 1H), 7.38-7.42 (m, 1H), 7.45-7.52 (m, 2H), 7.52 (bs, 1H), 7.68-7.74 (m, 1H), 8.16-8.20 (m, 1H).

Intermediate 15: 3-(((3-(Chloromethyl)-1-methyl-1H-pyrazol-5-yl)methyl)thio)naphthalen-1-yl acetate

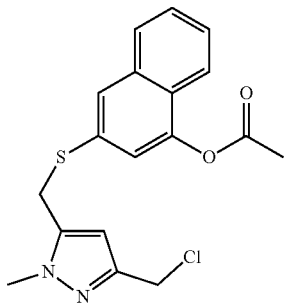 [SMILES: CC(=O)Oc1cc(SCc2cc(CCl)nn2C)cc2ccccc12]

Acetic anhydride (3.65 kg, 35.8 mol) was gradually charged to a stirring mixture of 3-(((3-(chloromethyl)-1-methyl-1H-pyrazol-5-yl)methyl)thio)naphthalen-1-ol (Intermediate 14, 9.51 kg, 95.3 wt %, 28.4 mol), DMAP (360 g, 2.95 mol) and MeCN (95 L) while keeping the temperature below 25° C. The mixture was stirred for 2 h at 15-20° C. EtOAc (95 L) was then added, followed by aq. NaCl (10 wt %, 95 L). After thorough mixing, the lower layer was removed. The upper layer was washed with two further portions of aq. NaCl (10 wt %, 95 L per portion) and then three cycles of vacuum distilling at below 40° C. to less than 29 L and then adding MTBE (95 L) were carried out. The mixture was vacuum distilled at below 40° C. to less than 48 L, stirred for at least 1 h at about 20° C., then cooled to 0-5° C. Heptane (95 L) was slowly added and the slurry was stirred at 0-5° C. for at least 1 h before filtering. The filter cake was washed with heptane (17 L) and then dried in a 35-40° C. vacuum oven to give 3-(((3-(chloromethyl)-1-methyl-1H-pyrazol-5-yl)methyl)thio)naphthalen-1-yl acetate (Intermediate 15, 8.67 kg, 96.1 wt %, 81%); m/z (ES+), [M+H]$^+$=361. $^1$H NMR (500 MHz, CDCl$_3$, 27° C.) δ 2.46 (s, 3H), 3.82 (s, 3H), 4.11 (s, 2H), 4.49 (s, 2H), 6.10 (s, 1H), 7.19 (d, 1H), 7.48-7.55 (m, 2H), 7.65-7.67 (m, 1H), 7.73-7.79 (m, 1H), 7.79-7.85 (m, 1H).

Intermediate 16: 3-(((3-((Acetylthio)methyl)-1-methyl-1H-pyrazol-5-yl)methyl)thio)naphthalen-1-yl acetate

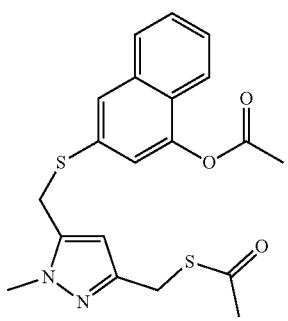 [SMILES: CC(=O)Oc1cc(SCc2cc(CSC(C)=O)nn2C)cc2ccccc12]

Potassium thioacetate (4.15 kg, 36.3 mol) was added to a mixture of 3-(((3-(chloromethyl)-1-methyl-1H-pyrazol-5-yl)methyl)thio)naphthalen-1-yl acetate (Intermediate 15, 8.62 kg, 96.1 wt %, 23.0 mol) and MeCN (86 L) while keeping the temperature below 25° C. The mixture was stirred for 3 h at 15-20° C. EtOAc (86 L) was then added, followed by water (86 L). After thorough mixing, the lower layer was removed. The upper layer was washed with two portions of aq. NaCl (15 wt %, 86 L per portion) and then four cycles of vacuum distilling at below 40° C. to less than 29 L and then adding MTBE (86 L×3 and 60 L on final cycle) were carried out. The mixture was stirred at 30-35° C. for at least 1 h, cooled to and then stirred at below 10° C. for at least 1 h, then heptane (86 L) was slowly added. The slurry was cooled to and held at 0-5° C. for at least 1 h before filtering. The filter cake was washed with heptane (17 L) and then dried in a 35-40° C. vacuum oven to give 3-(((3-((acetylthio)methyl)-1-methyl-1H-pyrazol-5-yl)methyl)thio)naphthalen-1-yl acetate (Intermediate 16, 8.44 kg, 97 wt %, 89%); m/z (ES+), [M+H]$^+$=401. $^1$H NMR (500 MHz, DMSO-d$_6$, 27° C.) δ 2.28 (s, 3H), 2.45 (s, 3H), 3.75 (s, 3H), 3.91 (s, 2H), 4.42 (s, 2H), 6.04 (s, 1H), 7.36 (d, 1H), 7.53 (ddd, 1H), 7.58 (ddd, 1H), 7.82 (d, 1H), 7.85 (d, 1H), 7.90 (d, 1H).

Intermediate 17: (R$_a$)-(+)-methyl 17-chloro-5,13,14,22-tetramethyl-28-oxa-2,9-dithia-5,6,12,13,22-pentaazaheptacyclo[27.7.1.1$^{4,7}$.0$^{1,15}$.0$^{16,21}$.0$^{20,24}$.0$^{30,35}$]octatriaconta-1(37),4(38),6,11,14,16,18,20,23,29,31,33,35-tridecaene-23-carboxylate

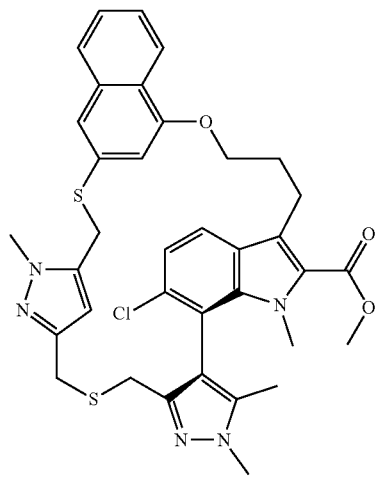

A solution of methanesulfonic anhydride (1.20 kg, 6.89 mol) in MeCN (2.5 L) was added to a solution of (R$_a$)-methyl 6-chloro-7-(3-(hydroxymethyl)-1,5-dimethyl-1H-pyrazol-4-yl)-3-(3-hydroxypropyl)-1-methyl-1H-indole-2-carboxylate (Intermediate 9, 1.19 kg, 97.6 wt %, 2.86 mol) and N,N-diisopropylethylamine (1.5 L, 8.6 mol) in THF (8.7 L) over 15 min at 0-30° C., followed by an MeCN (0.3 L) line wash. The resulting solution was agitated at 20° C. for 5 h before cooling to approximately −5° C. Meanwhile, a LiI (1.53 kg, 11.4 mol) solution was prepared by its portionwise addition (0.25 kg per portion) to MeCN (13 L) at below 30° C. The LiI solution was gradually added to the mesylation reaction mixture over 20 min at approximately −5° C., followed by an MeCN (1.2 L) line wash. The resulting slurry was warmed to 5° C. and stirred at that temperature for 5 h before cooling to approximately −15° C. and holding for 16 h. Toluene (5.8 L), water (11.6 L) and then a solution of hydrochloric acid (37 wt %, 0.23 L, 2.8 mol) in water (1.1 L) were sequentially added, followed by a water (0.12 L) line wash. The temperature of the reaction mixture remained at or below −9° C. throughout the additions. The lower layer was removed and water (11.6 L) was added to the upper layer and the resulting mixture was agitated and heated to 0° C. The lower layer was removed and the upper layer was washed twice more with water (11.6 L per wash) at approximately 0° C., mixing well before settling and removing the lower layer each time. The washed solution remaining in the reactor was then concentrated by distilling off solvent (8 L) under reduced pressure (210 to 250 mbar, 30° C. to 52° C.), before diluting with MeCN (2.9 L) and refluxing for 30 min at 500 mbar in order to thoroughly degas the solution. It was then cooled and held at 0° C. for 69 h (over weekend) before repeating the reduced pressure reflux under nitrogen in case of any air ingress during the long hold. This solution of methyl 6-chloro-7-[3-(iodomethyl)-1,5-dimethyl-pyrazol-4-yl]-1-methyl-3-(3-methylsulfonyloxypropyl)indole-2-carboxylate was then cooled to −14° C.

In parallel, a mixture of 3-(((3-((acetylthio)methyl)-1-methyl-1H-pyrazol-5-yl)methyl)thio)naphthalen-1-yl acetate (Intermediate 16, 1.40 kg, 97.8 wt %, 3.42 mol) and MeOH (7.25 L) was heated to reflux and held refluxing under nitrogen for 30 min before cooling to 0° C. Methanolic sodium methoxide (25 wt %, 1.6 L, 7.0 mol) was then added gradually over 10 min, before warming the resulting solution to 20° C. and holding there for 1.7 h. A portion of this solution (approx. 0.35 M; 6.6 L, approx. 2.3 mol) was gradually added to the solution of methyl 6-chloro-7-[3-(iodomethyl)-1,5-dimethyl-pyrazol-4-yl]-1-methyl-3-(3-methylsulfonyloxypropyl)indole-2-carboxylate from above at approximately −15° C. over 20 min. The resulting mixture was held at −10° C. for 1.4 h. Another portion of the disodium 3-(((1-methyl-3-(sulfidomethyl)-1H-pyrazol-5-yl)methyl)thio)naphthalen-1-olate solution (approx. 0.35 M; 1.5 L, approx. 0.53 mol) was added before holding the reaction mixture at −10° C. for 18 h. The mixture was warmed to 20° C. and removed from the reaction vessel, followed by a MeOH (0.6 L) rinse. DMSO was charged and it was heated with stirring to 100° C. Then the intermediate solution (approx. 15 L) was pumped back into the reactor over 2.8 h at 100° C., followed by a DMSO (0.6 L) rinse. After holding the reaction mixture at 100° C. for 0.8 h and then cooling it to just below 60° C., toluene (29 L) and water (5.8 L) were added. The mixture's temperature was adjusted to 50° C. and then a mixture of aq. NaOH (50 wt %, 160 g, 2.02 mol) and water (0.9 L), followed by a water (0.12 L) rinse, was added. After 10 min, the lower layer was removed. The upper layer was washed with a solution of NaCl (1.74 kg) in water (18.6 L) at 53° C. and then concentrated by distilling off solvent (6 L) at 160 mbar and jacket temperature 85° C. to give a toluene solution of the crude product (19.2 kg, 6.1 wt %, 1.7 mol). It was combined with another such solution (18.6 kg, 5.7 wt %, 1.5 mol) prepared from $(R_a)$-methyl 6-chloro-7-(3-(hydroxymethyl)-1,5-dimethyl-1H-pyrazol-4-yl)-3-(3-hydroxypropyl)-1-methyl-1H-indole-2-carboxylate (Intermediate 9, 1.19 kg, 98.0 wt %, 2.87 mol) by following the same procedure. The combined solution was purified portion-wise (0.84 L per portion, 51 portions) by chromatography on a compressed column (20 cm diameter×22 cm long) of Kromasil® silica (3.0 kg, 10 µm particle size, 60 Å pore size), eluting with a mixture of toluene and ethanol (approximate volume ratio 93% toluene:7% ethanol). The product fractions were evaporated under reduced pressure at 50° C. in two parts until distillation ceased, to give the product (91 g and 2.40 kg) as a foam. The batches were dissolved in DMSO (148 g and 3.22 kg) to give DMSO solutions of $(R_a)$-(+)-methyl 17-chloro-5,13,14,22-tetramethyl-28-oxa-2,9-dithia-5,6,12, 13,22-pentaazaheptacyclo[27.7.1.1$^{4,7}$.0$^{11,15}$.0$^{16,21}$.0$^{20,24}$. 0$^{30,35}$]octatriaconta-1(37),4(38),6,11,14,16,18,20,23,29,31, 33,35-tridecaene-23-carboxylate (Intermediate 17, 239 g, 32.2 wt %, 0.112 mol and 5.63 kg, 37.9 wt %, 3.11 mol) in combined 56% yield; m/z (ES+), [M+H]$^+$=686. $^1$H NMR (500 MHz, DMSO-d$_6$, 27° C.) δ 1.97 (s, 3H), 2.16-2.27 (m, 1H), 2.32-2.42 (m, 1H), 2.89 (d, 1H), 3.08 (d, 1H), 3.07-3.14 (m, 1H), 3.16 (d, 1H), 3.36-3.42 (m, 1H), 3.43 (d, 1H), 3.48 (s, 3H), 3.69 (s, 3H), 3.76 (s, 3H), 3.77-3.83 (m, 1H), 3.84 (s, 3H), 4.13 (td, 1H), 4.22 (d, 1H), 4.29 (d, 1H), 4.77 (s, 1H), 6.65 (d, 1H), 7.18 (d, 1H), 7.39-7.40 (m, 1H), 7.44-7.48 (m, 1H), 7.47-7.51 (m, 1H), 7.71-7.74 (m, 1H), 7.90 (d, 1H), 8.08-8.12 (m, 1H).

Compound 1: $(R_a)$-(+)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid

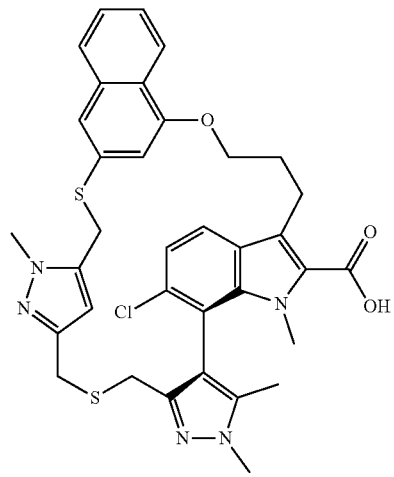

$(R_a)$-(+)-methyl 17-chloro-5,13,14,22-tetramethyl-28-oxa-2,9-dithia-5,6,12,13,22-pentaazaheptacyclo[27.7.1.1$^{4,7}$. 0$^{11,15}$.0$^{16,21}$.0$^{20,24}$.0$^{30,35}$]octatriaconta-1(37),4(38),6,11,14, 16,18,20,23,29,31,33,35-tridecaene-23-carboxylate (Intermediate 17, 37.9 wt % in DMSO containing 57.3 wt % DMSO; 2.81 kg, 1.55 mol), DMSO (2.81 kg) and ethanol (1.68 kg) were charged to a 20 L reactor and the solution was heated with stirring to 50° C. NaOH (50 wt % in water; 186 g, 2.33 mol), followed by a water (267 mL) line wash, was then added. After 1.5 h, acetic acid (267 mL, 4.66 mol) was added. Aqueous ethanol (34.5 wt %; 3.0 L) was then added, followed by a Form A $(R_a)$-(+)-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37), 4(38),6,11,14,16,18,20,23,29,31,33,35-tridecaene-23-carboxylic acid monohydrate (0.8 g, 0.001 mol) crystallisation seed. The mixture was agitated at 50° C. for 4.5 h, then two more portions (4.2 and 1.3 L) of aqueous ethanol (34.5 wt %) were gradually added (over 4.1 and 0.7 h respectively). The slurry was cooled to 20° C. over 2 h and held at 20° C. for 17 h. The slurry was filtered under suction and the filter cake was washed twice with aqueous ethanol (34.5 wt %; 2.7 L per wash) before drying in a 40° C. vacuum oven to give Form A $(R_a)$-(+)-17-chloro-5,13,14, 22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate (Compound 1, 1.01 kg, 99.4 wt %, >99.9% e.e., 94%); m/z (ES+), [M+H]$^+$=672. $^1$H NMR (500 MHz, DMSO-d$_6$, 27° C.) δ 1.96 (s, 3H), 2.16-2.28 (m, 1H), 2.30-2.42 (m, 1H), 2.88 (d, 1H), 3.06 (ddd, 1H), 3.12 (d, 1H), 3.18 (d, 1H), 3.42 (d, 1H), 3.41-3.48 (m, 1H), 3.51 (s, 3H), 3.72 (s, 3H), 3.75 (s, 3H), 3.84 (td, 1H), 4.09 (td, 1H), 4.25 (d, 1H), 4.28 (d, 1H), 4.75 (s, 1H), 6.67 (d, 1H), 7.13 (d, 1H), 7.37-7.40 (m, 1H), 7.43-7.47 (m, 1H), 7.45-7.50 (m, 1H), 7.68-7.74 (m, 1H), 7.84 (d, 1H), 8.07-8.13 (m, 1H), 13.36 (bs, 1H).

Chiral purity analysis HPLC method details: column=ChiralPak IE-3, 3 μm 4.6×250 mm; temperature=40° C.; mobile phase=50:50 ethanol:hexane by volume containing 0.1% TFA, flowing at 0.8 mL/min; detection by UV at 305 nm; inj. volume=10 μL (this may be adjusted to achieve a suitable limit of detection); retention times 8.5 and 11.5 min for the R$_a$ and S$_a$ enantiomers respectively.

The XRPD of Form A is shown in FIG. 1 and the results are tabulated below (Table 1).

TABLE 2

XRPD Peaks for Form A

| Angle (2θ ± 0.2°) | Intensity (%) |
|---|---|
| 18.2 | 100.0 |
| 12.5 | 87.7 |
| 14.4 | 82.7 |
| 8.4 | 75.8 |
| 17.2 | 70.4 |
| 26.8 | 64.4 |
| 10.7 | 59.0 |
| 27.7 | 55.9 |
| 30.2 | 45.6 |
| 23.0 | 42.0 |
| 20.5 | 40.5 |
| 19.2 | 39.4 |
| 7.0 | 35.9 |
| 25.0 | 35.3 |
| 17.6 | 34.5 |
| 23.7 | 34.4 |
| 19.8 | 33.4 |
| 24.5 | 31.8 |
| 22.0 | 30.9 |
| 20.9 | 30.8 |
| 24.2 | 28.8 |
| 37.6 | 27.1 |
| 31.5 | 26.9 |
| 22.3 | 26.5 |
| 13.9 | 25.3 |
| 13.7 | 23.9 |
| 29.0 | 23.9 |
| 34.5 | 22.9 |
| 26.3 | 21.3 |
| 13.1 | 20.8 |
| 29.4 | 20.7 |
| 15.6 | 19.8 |
| 36.9 | 17.9 |
| 15.1 | 17.9 |
| 36.4 | 16.7 |
| 32.8 | 16.6 |
| 38.2 | 16.2 |
| 28.6 | 16.1 |
| 35.5 | 14.9 |

Figure 2:
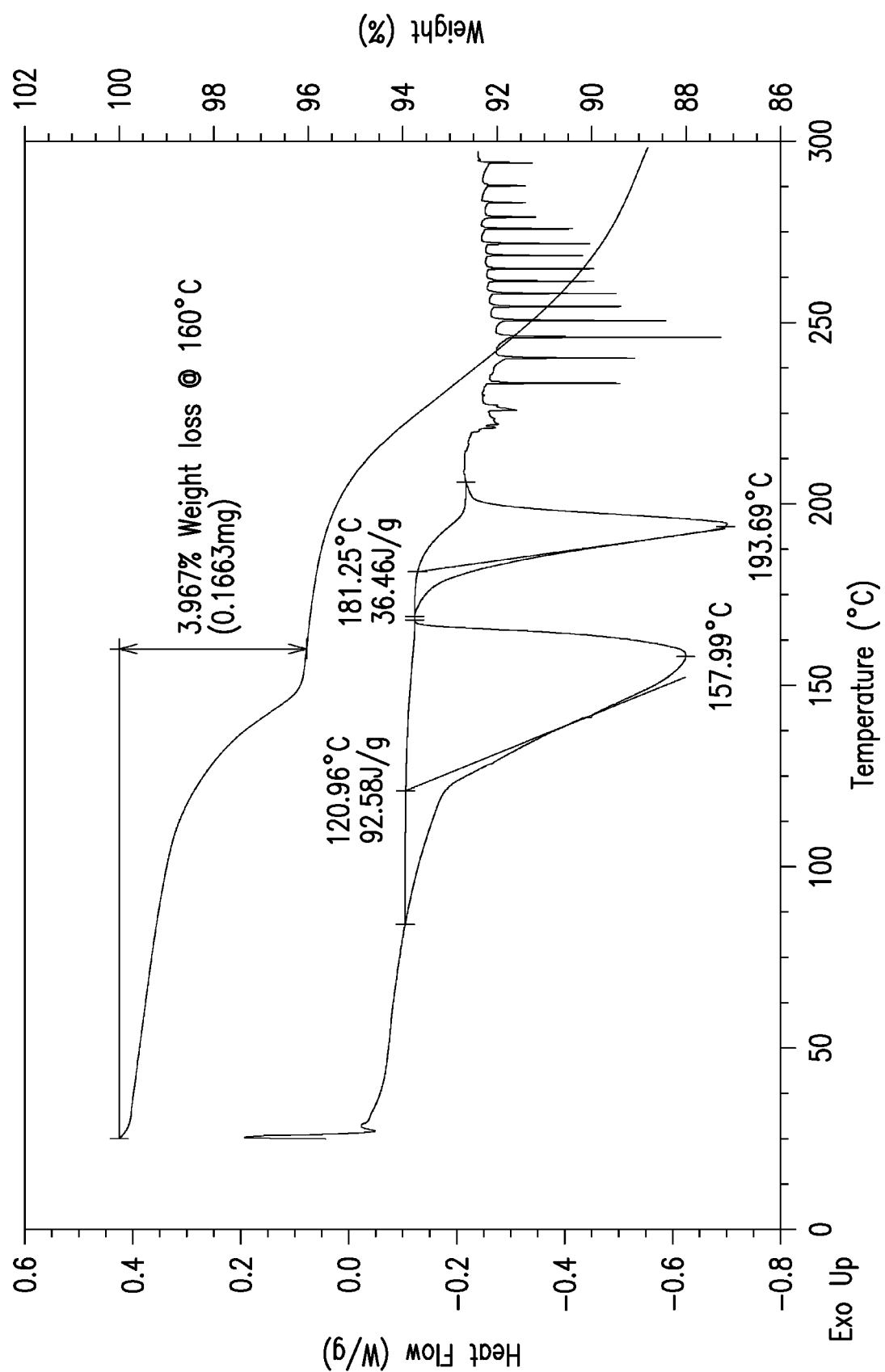
FIG. 2 illustrates the differential scanning calorimetry (DSC) and thermogravimetric analysis (TGA) traces of Form A $(R_a)$-17-chloro-5,13,14,22-tetramethyl-28-oxa-2,9-dithia-5,6,12,13,22-pentaazaheptacyclo[27.7.1.1$^{4,7}$.0$^{11,15}$.0$^{16,21}$.0$^{20,24}$.0$^{30,35}$]octatriaconta-1(37),4(38),6,11,14,16,18,20,23,29,31,33,35-tridecaene-23-carboxylic acid monohydrate.

DSC analysis indicated that Form A has an endotherm event of desolvation with an onset at about 121° C. and a peak at about 158° C., followed by an endotherm event of melting/decomposition with an onset at about 181° C. and a peak at about 194° C. TGA indicated that Form A exhibits a mass loss of about 4.0% upon heating from about 25° C. to about 160° C. A representative DSC/TGA thermogram of Form A is shown in FIG. 2.

Single crystal structure analysis confirmed that Form A is a monohydrate form. Crystallographic data: Space group monoclinic P2(1), unit cell dimensions: a=13.83(3) Å, b=7.578(14) Å, c=33.57(6) Å, β=90.23(2°), V=3518(12) Å$^3$.

X-Ray Powder Diffraction (XRPD) Analysis

XRPD analysis was performed using a Bruker D4 diffractometer, which is commercially available from Bruker AXS Inc™ (Madison, Wis.). The XRPD spectra were obtained by mounting a sample (approximately 20 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (i.e., about 1.54 angstroms). The sample was exposed for 1 second per 0.02 degree 2-theta increment (continuous scan mode) over the range 2 degrees to 40 degrees 2-theta in theta-theta mode. The running time was 31 min, 41 s.

XRPD 2θ values may vary with a reasonable range, e.g., in the range ±0.2° and that XRPD intensities may vary when measured for essentially the same crystalline form for a variety of reasons including, for example, preferred orientation. Principles of XRPD are described in publications, such as, for example, Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; and Klug, H. P. & Alexander, L. E. (1974), X-ray Diffraction Procedures, John Wiley and Sons, New York.

DSC Analysis

DSC analysis was performed on samples prepared according to standard methods using a Q SERIES™ Q1000 DSC calorimeter available from TA INSTRUMENTS® (New Castle, Del.). A sample (approximately 2 mg) was weighed into an aluminum sample pan and transferred to the DSC. The instrument was purged with nitrogen at 50 mL/min and data collected between about 22° C. and 300° C., using a dynamic heating rate of about 10° C./minute. Thermal data was analyzed using standard software, e.g., Universal v.4.5 Å from TA INSTRUMENTS®.

Thermogravimetry Analysis (TGA)

TGA was performed on samples prepared according to standard methods using a Q SERIES™ Q5000 thermogravimetry analyzer available from TA Instruments INSTRUMENTS® (New Castle, Del.). A sample (approximately 5 mg) was placed into an aluminum sample pan and transferred to the TGA furnace. The instrument was purged with nitrogen at 50 mL/min and data collected between 25° C. and 300° C., using a dynamic heating rate of 10° C./minute. Thermal data was analyzed using standard software, e.g., Universal v.4.5 Å from TA INSTRUMENTS®.

Example 1: In Vitro Activity of Compound 1

Caspase Activity assay: This is a cell assay to measure the induction of apoptosis in MOLP-8 (multiple myeloma), KMS-12-BM (multiple myeloma), MV4; 11 (acute myeloid leukemia), and NCI-H23 (non-small cell lung cancer) cells after 6 h treatment with Mcl-1 inhibitors. On the first day, 3000 (MOLP-8, KMS-12-BM, MV4; 11) or 1250 (NCI-H23) cells/well were seeded with 50 μL of growth media (IMDM+10% FBS+2 mM L-Glu for MV4; 11 and RPMI-1640+10% FBS+2 mM L-Glu for all others) in 384-well white microplates, and incubated overnight (37° C., 5% CO$_2$, 80% RH). On the second day, the cells were treated with Compound I using an ECHO acoustic liquid handler (10 point half-log serial dilution, 31.5 μM top concentration, 0.3% final DMSO concentration). After 6 h incubation (37° C., 5% CO$_2$, 80% RH), 25 μL of Caspase-Glo 3/7 reagent (Promega) was added into each well, and plates were incubated at room temperature for 30 min protected from light. Luminescence was recorded using an Infinite M200 microplate reader (Tecan) with a 100 ms integration time. EC$_{50}$ values were calculated using GeneData analysis software and are shown in Table 2, below.

TABLE 2

Results from in vitro Caspase Activity assay

| Cell Line | Compound I Caspase Activity, EC$_{50}$ (nM) |
|---|---|
| MOLP-8 | 30 |
| KMS-12-BM | 43 |
| MV4; 11 | 20 |
| NCI-H23 | 193 |

The invention claimed is:
1. A compound selected from:

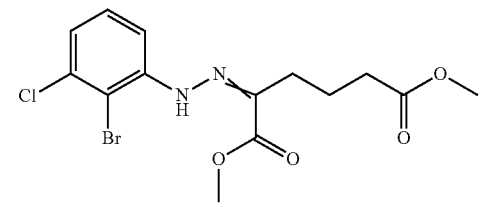

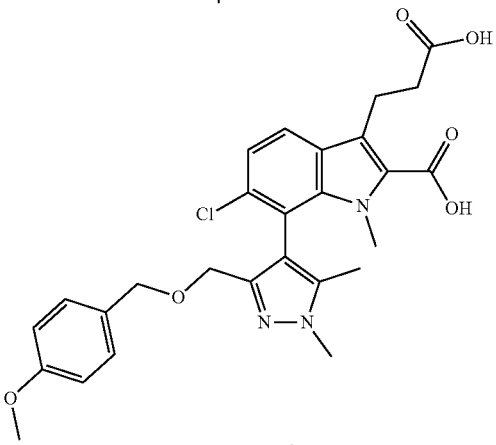

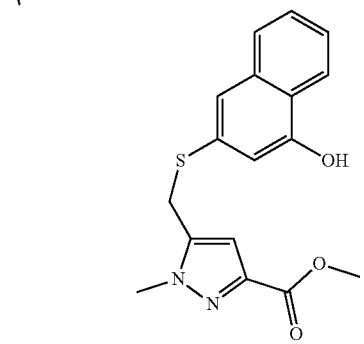

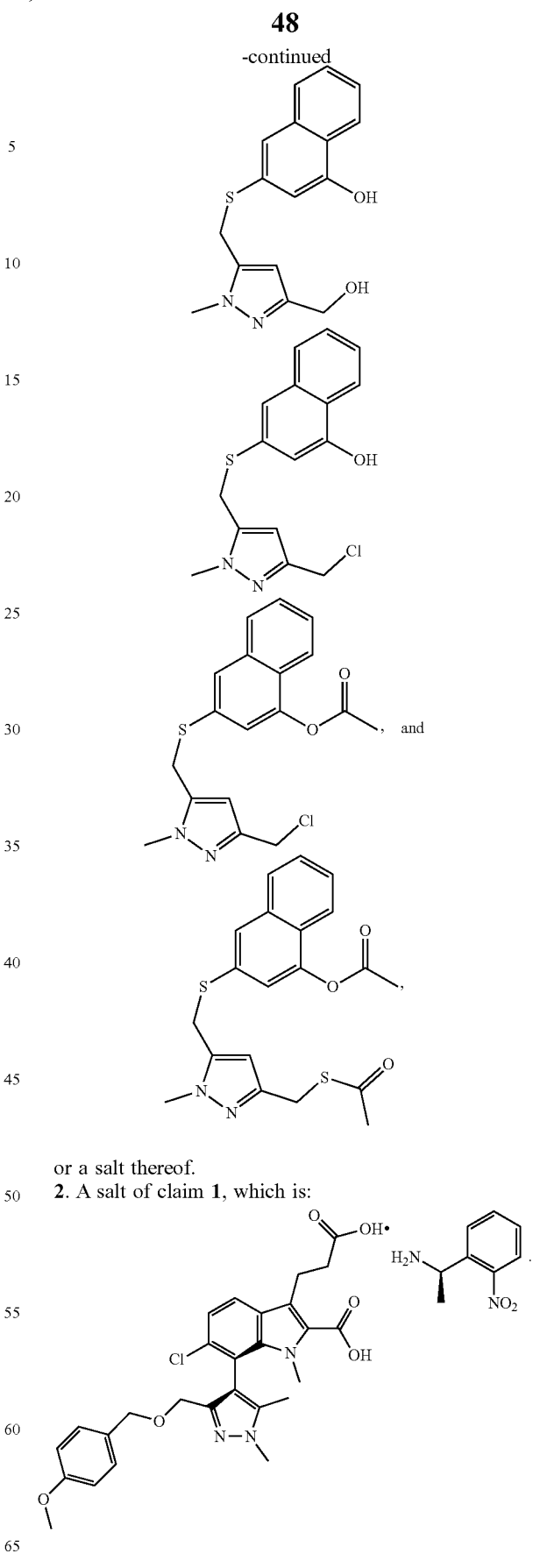

or a salt thereof.

2. A salt of claim 1, which is:

* * * * *